(12) United States Patent
Cagle et al.

(10) Patent No.: US 11,564,764 B2
(45) Date of Patent: Jan. 31, 2023

(54) CART FOR ROBOTIC ARMS AND METHOD AND APPARATUS FOR REGISTERING CART TO SURGICAL TABLE

(71) Applicant: Verb Surgical Inc., Santa Clara, CA (US)

(72) Inventors: David James Cagle, Belmont, CA (US); Wayne Grout, San Francisco, CA (US); Karen Shakespear Koenig, San Jose, CA (US); Bernard Fai Kin Siu, San Jose, CA (US); Jose Luis Cordoba, Malaga (ES)

(73) Assignee: VERB SURGICAL INC., Santa Clara, CA (US)

( * ) Notice: Subject to any disclaimer, the term of this patent is extended or adjusted under 35 U.S.C. 154(b) by 8 days.

(21) Appl. No.: 17/067,527

(22) Filed: Oct. 9, 2020

(65) Prior Publication Data

US 2021/0022822 A1   Jan. 28, 2021

Related U.S. Application Data

(63) Continuation of application No. 15/785,331, filed on Oct. 16, 2017, now Pat. No. 10,856,948.
(Continued)

(51) Int. Cl.
*G01S 3/80* (2006.01)
*A61B 50/13* (2016.01)
(Continued)

(52) U.S. Cl.
CPC .............. *A61B 50/13* (2016.02); *A61B 34/30* (2016.02); *A61B 90/50* (2016.02); *B25J 9/0009* (2013.01);
(Continued)

(58) Field of Classification Search
CPC ......... A61B 50/13; A61B 34/30; A61B 90/50; B25J 9/0009; F21V 23/0442
(Continued)

(56) References Cited

U.S. PATENT DOCUMENTS 5,351,676 A   10/1994   Putman
5,876,325 A   3/1999   Mizuno et al.
(Continued)

FOREIGN PATENT DOCUMENTS

AU   2020260428 A1   11/2020
CA       2913943 A1   12/2014
(Continued)

OTHER PUBLICATIONS

Decision of Refusal of the Japanese Patent Office dated Mar. 30, 2021 for related Japanese Patent Application No. 2019-563192.
(Continued)

*Primary Examiner* — Todd M Epps
(74) *Attorney, Agent, or Firm* — Womble Bond Dickinson (US) LLP

(57) ABSTRACT

In some embodiments, an apparatus can include a cart for a surgical robotic arm having a coupler releasably coupleable to a coupling site on a surgical table. The cart can include a base and a first engagement feature. The base can be freely movably on a support surface between a first location remote from the surgical table and a second location adjacent the surgical table. The first engagement feature can be configured for engagement with a second engagement feature associated with the surgical table such that, when the first engagement feature and the second engagement feature are engaged, the coupler of the robotic am is disposed in a position in which the coupler of the robotic arm can be engaged by the coupler of the surgical table.

21 Claims, 21 Drawing Sheets

Related U.S. Application Data

(60) Provisional application No. 62/513,327, filed on May 31, 2017.

(51) Int. Cl.
*A61B 90/50* (2016.01)
*A61B 34/30* (2016.01)
*B25J 9/00* (2006.01)
*F21V 23/04* (2006.01)
*A61B 90/57* (2016.01)
*A61B 90/00* (2016.01)
*A61B 17/00* (2006.01)

(52) U.S. Cl.
CPC *F21V 23/0442* (2013.01); *A61B 2017/00477* (2013.01); *A61B 2090/0807* (2016.02); *A61B 2090/571* (2016.02); *A61B 2560/0437* (2013.01)

(58) Field of Classification Search
USPC ........ 248/645; 362/459, 486, 257, 285, 383, 362/382, 384
See application file for complete search history.

(56) References Cited

U.S. PATENT DOCUMENTS

| | | |
|---|---|---|
| 5,878,193 A | 3/1999 | Wang et al. |
| 6,132,368 A | 10/2000 | Cooper |
| 6,246,200 B1 | 6/2001 | Blumenkranz et al. |
| 6,330,890 B1 | 12/2001 | Ekman |
| 6,331,181 B1 | 12/2001 | Tierney et al. |
| 6,346,072 B1 | 2/2002 | Cooper |
| 6,450,978 B1 | 9/2002 | Brosseau et al. |
| 6,451,027 B1 | 9/2002 | Cooper et al. |
| 6,535,756 B1 | 3/2003 | Simon et al. |
| 6,587,750 B2 | 7/2003 | Gerbi et al. |
| 6,608,628 B1 | 8/2003 | Ross et al. |
| 6,659,939 B2 | 12/2003 | Moll et al. |
| 6,768,496 B2 | 7/2004 | Bieger et al. |
| 6,788,018 B1 | 9/2004 | Blumenkranz |
| 6,866,671 B2 | 3/2005 | Tierney et al. |
| 6,920,347 B2 | 7/2005 | Simon et al. |
| 6,962,581 B2 | 11/2005 | Thoe |
| 6,995,744 B1 | 2/2006 | Moore et al. |
| 7,008,362 B2 | 3/2006 | Fitzgibbon |
| 7,012,203 B2 | 3/2006 | Hanson et al. |
| 7,048,745 B2 | 5/2006 | Tierney et al. |
| 7,206,627 B2 | 4/2007 | Abovitz et al. |
| 7,217,269 B2 | 5/2007 | El-Galley et al. |
| 7,277,120 B2 | 10/2007 | Gere et al. |
| 7,317,955 B2 | 1/2008 | McGreevy |
| 7,331,967 B2 | 2/2008 | Lee et al. |
| 7,357,774 B2 | 4/2008 | Cooper |
| 7,369,116 B2 | 5/2008 | Logue |
| 7,379,790 B2 | 5/2008 | Toth et al. |
| 7,498,532 B2 | 3/2009 | Kuhner et al. |
| 7,524,320 B2 | 4/2009 | Tierney et al. |
| 7,554,526 B2 | 6/2009 | Logue |
| 7,594,912 B2 | 9/2009 | Cooper et al. |
| 7,666,191 B2 | 2/2010 | Orban et al. |
| 7,699,855 B2 | 4/2010 | Anderson et al. |
| 7,727,244 B2 | 6/2010 | Orban et al. |
| 7,768,702 B2 | 8/2010 | Hirose et al. |
| 7,781,941 B2 | 8/2010 | Horvath et al. |
| 7,783,133 B2 | 8/2010 | Dunki-Jacobs et al. |
| 7,789,874 B2 | 9/2010 | Yu et al. |
| 7,789,875 B2 | 9/2010 | Brock et al. |
| 7,819,885 B2 | 10/2010 | Cooper |
| 7,840,042 B2 | 11/2010 | Kriveshko et al. |
| 7,843,158 B2 | 11/2010 | Prisco |
| 7,853,305 B2 | 12/2010 | Simon et al. |
| 7,865,266 B2 | 1/2011 | Moll et al. |
| 7,883,458 B2 | 2/2011 | Hamel |
| 7,907,166 B2 | 3/2011 | Lamprecht et al. |
| 7,922,439 B2 | 4/2011 | Kato |
| 7,947,050 B2 | 5/2011 | Lee et al. |
| 7,955,322 B2 | 6/2011 | Devengenzo et al. |
| 7,983,793 B2 | 7/2011 | Toth et al. |
| 8,004,229 B2 | 8/2011 | Nowlin et al. |
| 8,062,288 B2 | 11/2011 | Cooper et al. |
| 8,079,950 B2 | 12/2011 | Stern et al. |
| 8,086,008 B2 | 12/2011 | Coste-Maniere et al. |
| 8,095,200 B2 | 1/2012 | Quaid, III |
| 8,100,133 B2 | 1/2012 | Mintz et al. |
| 8,105,338 B2 | 1/2012 | Anderson et al. |
| 8,120,301 B2 | 2/2012 | Goldberg et al. |
| 8,126,114 B2 | 2/2012 | Naylor et al. |
| 8,131,031 B2 | 3/2012 | Lloyd |
| 8,142,447 B2 | 3/2012 | Cooper et al. |
| 8,147,503 B2 | 4/2012 | Zhao |
| 8,155,479 B2 | 4/2012 | Hoffman et al. |
| 8,190,238 B2 | 5/2012 | Moll et al. |
| 8,202,278 B2 | 6/2012 | Orban et al. |
| 8,206,406 B2 | 6/2012 | Orban, III |
| 8,256,319 B2 | 9/2012 | Cooper et al. |
| 8,332,072 B1 | 12/2012 | Schaible et al. |
| 8,391,954 B2 | 3/2013 | Quaid, III |
| 8,395,342 B2 | 3/2013 | Prisco |
| 8,398,541 B2 | 3/2013 | Dimaio et al. |
| 8,418,073 B2 | 4/2013 | Mohr et al. |
| 8,469,947 B2 | 6/2013 | Devengenzo et al. |
| 8,473,031 B2 | 6/2013 | Nixon et al. |
| 8,496,647 B2 | 7/2013 | Blumenkranz et al. |
| 8,504,136 B1 | 8/2013 | Sun et al. |
| 8,506,555 B2 | 8/2013 | Ruiz Morales |
| 8,508,173 B2 | 8/2013 | Goldberg et al. |
| 8,521,331 B2 | 8/2013 | Itkowitz |
| 8,527,094 B2 | 9/2013 | Kumar et al. |
| 8,541,970 B2 | 9/2013 | Nowlin et al. |
| 8,562,594 B2 | 10/2013 | Cooper et al. |
| 8,594,841 B2 | 11/2013 | Zhao |
| 8,600,551 B2 | 12/2013 | Itkowitz et al. |
| 8,620,473 B2 | 12/2013 | Diolaiti et al. |
| 8,624,537 B2 | 1/2014 | Nowlin et al. |
| 8,628,518 B2 | 1/2014 | Blumenkranz et al. |
| 8,634,957 B2 | 1/2014 | Toth et al. |
| 8,638,056 B2 | 1/2014 | Goldberg et al. |
| 8,672,922 B2 | 3/2014 | Loh et al. |
| 8,682,489 B2 | 3/2014 | Itkowitz et al. |
| 8,706,184 B2 | 4/2014 | Mohr et al. |
| 8,715,167 B2 | 5/2014 | Stern et al. |
| 8,747,288 B2 | 6/2014 | Strotzer et al. |
| 8,749,189 B2 | 6/2014 | Nowlin et al. |
| 8,749,190 B2 | 6/2014 | Nowlin et al. |
| 8,761,337 B2 | 6/2014 | Naylor et al. |
| 8,786,241 B2 | 7/2014 | Nowlin et al. |
| 8,806,359 B2 | 8/2014 | Garibaldi et al. |
| 8,816,628 B2 | 8/2014 | Nowlin et al. |
| 8,823,308 B2 | 9/2014 | Nowlin et al. |
| 8,828,023 B2 | 9/2014 | Neff et al. |
| 8,831,782 B2 | 9/2014 | Itkowitz |
| 8,870,861 B2 | 10/2014 | El-Galley et al. |
| 8,888,764 B2 | 11/2014 | Devengenzo et al. |
| 8,930,027 B2 | 1/2015 | Schaible et al. |
| 8,939,500 B2 | 1/2015 | Voigt et al. |
| 8,968,333 B2 | 3/2015 | Yu et al. |
| 8,989,903 B2 | 3/2015 | Weir et al. |
| 8,996,173 B2 | 3/2015 | Itkowitz et al. |
| 9,002,517 B2 | 4/2015 | Bosscher et al. |
| 9,026,247 B2 | 5/2015 | White et al. |
| 9,078,686 B2 | 7/2015 | Schena |
| 9,108,318 B2 | 8/2015 | Diolaiti |
| 9,129,422 B2 | 9/2015 | Mountney |
| 9,179,980 B2 | 11/2015 | Yoon |
| 9,198,731 B2 | 12/2015 | Balaji et al. |
| 9,215,293 B2 | 12/2015 | Miller |
| 9,221,172 B2 | 12/2015 | Williamson et al. |
| 9,232,984 B2 | 1/2016 | Guthart et al. |
| 9,241,768 B2 | 1/2016 | Sandhu et al. |
| 9,254,572 B2 | 2/2016 | Strotzer |
| 9,256,936 B2 | 2/2016 | Jacobs et al. |
| 9,259,276 B2 | 2/2016 | Mintz et al. |
| 9,259,282 B2 | 2/2016 | Azizian et al. |

(56) References Cited

U.S. PATENT DOCUMENTS

| | | | |
|---|---|---|---|
| 9,295,524 B2 | 3/2016 | Schena et al. | |
| 9,320,568 B2 | 4/2016 | Orban et al. | |
| 9,333,042 B2 | 5/2016 | Diolaiti et al. | |
| 9,345,546 B2 | 5/2016 | Toth et al. | |
| 9,433,288 B2 | 9/2016 | Voigt et al. | |
| 9,486,159 B2 | 11/2016 | Coste-Maniere et al. | |
| 9,694,839 B2 | 7/2017 | Canady et al. | |
| 10,034,721 B1 | 7/2018 | Timm et al. | |
| 10,333,296 B1 | 6/2019 | Wu et al. | |
| 10,485,623 B2 | 11/2019 | Wiggers | |
| 10,792,119 B2 | 10/2020 | Timm et al. | |
| 10,856,948 B2* | 12/2020 | Cagle | A61B 50/13 |
| 10,913,145 B2* | 2/2021 | Cagle | A61B 50/13 |
| 10,913,291 B2 | 2/2021 | Nishiura | |
| 2002/0133174 A1 | 9/2002 | Charles et al. | |
| 2004/0236175 A1 | 11/2004 | Boone et al. | |
| 2005/0206107 A1 | 9/2005 | Schubert et al. | |
| 2006/0161136 A1 | 7/2006 | Anderson et al. | |
| 2009/0068620 A1 | 3/2009 | Knobel et al. | |
| 2009/0240370 A1 | 9/2009 | Nichols et al. | |
| 2009/0248041 A1 | 10/2009 | Williams et al. | |
| 2010/0012798 A1 | 1/2010 | Blum et al. | |
| 2010/0243344 A1 | 9/2010 | Wyrobek et al. | |
| 2012/0154564 A1 | 6/2012 | Hoffman et al. | |
| 2013/0085389 A1 | 4/2013 | Tsang et al. | |
| 2013/0085510 A1 | 4/2013 | Stefanchik et al. | |
| 2014/0052154 A1 | 2/2014 | Griffiths et al. | |
| 2014/0100588 A1 | 4/2014 | Blumenkranz et al. | |
| 2014/0107627 A1 | 4/2014 | Blumenkranz et al. | |
| 2014/0130810 A1 | 5/2014 | Azizian et al. | |
| 2014/0168073 A1 | 6/2014 | Chizeck et al. | |
| 2014/0171965 A1 | 6/2014 | Loh et al. | |
| 2014/0188131 A1 | 7/2014 | Toth et al. | |
| 2014/0276949 A1 | 9/2014 | Staunton et al. | |
| 2014/0282196 A1 | 9/2014 | Zhao | |
| 2014/0297130 A1 | 10/2014 | Griffiths et al. | |
| 2015/0032126 A1 | 1/2015 | Nowlin et al. | |
| 2015/0045812 A1 | 2/2015 | Seo | |
| 2015/0051733 A1 | 2/2015 | Nowlin et al. | |
| 2015/0190201 A1 | 7/2015 | Olson | |
| 2015/0223897 A1 | 8/2015 | Kostrzewski et al. | |
| 2015/0265356 A1 | 9/2015 | Schena | |
| 2015/0321355 A1 | 11/2015 | Kishi | |
| 2015/0374446 A1 | 12/2015 | Malackowski et al. | |
| 2016/0076992 A1 | 3/2016 | Gillespie et al. | |
| 2016/0140875 A1 | 5/2016 | Kumar et al. | |
| 2016/0157943 A1 | 6/2016 | Mintz et al. | |
| 2016/0166345 A1 | 6/2016 | Kumar et al. | |
| 2016/0184037 A1 | 6/2016 | Cooper et al. | |
| 2016/0242860 A1 | 8/2016 | Diolaiti et al. | |
| 2017/0000575 A1 | 1/2017 | Griffiths et al. | |
| 2017/0065354 A1 | 3/2017 | Shiels et al. | |
| 2017/0065355 A1 | 3/2017 | Ross et al. | |
| 2017/0071692 A1 | 3/2017 | Taylor et al. | |
| 2017/0071693 A1 | 3/2017 | Taylor et al. | |
| 2017/0079730 A1 | 3/2017 | Azizian et al. | |
| 2017/0083453 A1 | 3/2017 | Guilford et al. | |
| 2017/0087730 A1 | 3/2017 | Robinson et al. | |
| 2017/0119421 A1 | 5/2017 | Staunton et al. | |
| 2017/0135771 A1 | 5/2017 | Auld et al. | |
| 2017/0245927 A1 | 8/2017 | Govari et al. | |
| 2017/0312047 A1 | 11/2017 | Swarup et al. | |
| 2018/0042682 A1 | 2/2018 | Iceman et al. | |
| 2018/0051850 A1 | 2/2018 | Bax et al. | |
| 2018/0078439 A1 | 3/2018 | Cagle et al. | |
| 2018/0078440 A1 | 3/2018 | Koenig et al. | |
| 2018/0147104 A1 | 5/2018 | Timm et al. | |
| 2018/0147105 A1 | 5/2018 | Timm et al. | |
| 2018/0147106 A1 | 5/2018 | Soundararajan et al. | |
| 2018/0207794 A1 | 7/2018 | Sebring et al. | |
| 2018/0271604 A1 | 9/2018 | Grout et al. | |
| 2018/0333215 A1 | 11/2018 | Timm et al. | |
| 2018/0344421 A1 | 12/2018 | Cagle et al. | |
| 2018/0361568 A1 | 12/2018 | Cagle et al. | |
| 2018/0362060 A1 | 12/2018 | Schaller et al. | |
| 2020/0000536 A1 | 1/2020 | Yakimovich et al. | |

FOREIGN PATENT DOCUMENTS

| | | |
|---|---|---|
| CN | 102006834 A | 4/2011 |
| CN | 103448643 A | 12/2013 |
| CN | 105163998 A | 12/2015 |
| CN | 105213030 A | 1/2016 |
| CN | 105310775 A | 2/2016 |
| CN | 205073024 U | 3/2016 |
| CN | 110868954 A | 3/2020 |
| CN | 110868956 A | 3/2020 |
| CN | 110913820 A | 3/2020 |
| EP | 0752237 A1 | 1/1997 |
| EP | 2145586 A1 | 1/2010 |
| EP | 2145596 A1 | 1/2010 |
| EP | 2893898 A1 | 7/2015 |
| EP | 2898898 A1 | 7/2015 |
| EP | 3600122 A1 | 2/2020 |
| JP | 61-173822 A | 8/1986 |
| JP | 02-059468 A | 2/1990 |
| JP | 04-019729 A | 1/1992 |
| JP | 06-297378 A | 10/1994 |
| JP | 08-224243 A | 9/1996 |
| JP | 2000-255428 A | 9/2000 |
| JP | 2007-276063 A | 10/2007 |
| JP | 2014-158942 A | 9/2014 |
| JP | 2017-513550 A | 6/2017 |
| KR | 10-2010-0067846 A | 6/2010 |
| KR | 10-2016-0135240 A | 11/2016 |
| RU | 122281 U1 | 11/2012 |
| WO | 2008103209 A1 | 8/2008 |
| WO | 2010/068005 A2 | 6/2010 |
| WO | 2014/151621 A1 | 9/2014 |
| WO | 2014/152694 A1 | 9/2014 |
| WO | 2014/201538 A1 | 12/2014 |
| WO | 2015/142798 A1 | 9/2015 |
| WO | 2015/142801 A1 | 9/2015 |
| WO | 2015/175203 A1 | 11/2015 |
| WO | 2016/048738 A1 | 3/2016 |
| WO | 2016/054256 A1 | 4/2016 |
| WO | 2016/058079 A1 | 4/2016 |
| WO | 2016/069661 A1 | 5/2016 |
| WO | 2017/030848 A1 | 2/2017 |
| WO | 2017/062391 A1 | 4/2017 |
| WO | 2017/083453 A1 | 5/2017 |
| WO | 2017/085094 A1 | 5/2017 |
| WO | 2018/053282 A1 | 3/2018 |
| WO | 2018/217518 A1 | 11/2018 |
| WO | 2018/222470 A1 | 12/2018 |
| WO | 2018/236594 A1 | 12/2018 |

OTHER PUBLICATIONS

Examination Search Report of the Canadian Patent Office dated Mar. 10, 2021 for related Canadian Patent Application No. 3060997.

First Office Action of the Chinese Patent Office dated Apr. 8, 2021 for related Chinese Patent Application No. 201880040951.8.

Non-Final Office Action of the U.S. Patent Office dated Mar. 23, 2021 for related U.S. Appl. No. 16/653,565.

Notice of Office Action of the Korean Patent Office dated Apr. 22, 2021 for related Korean Patent Application No. 10-2019-7034549.

Office Action of the Canadian Patent Office dated Apr. 19, 2021 for related Canadian Patent Application No. 3074438.

Search Report of the Chinese Patent Office dated Mar. 31, 2021 for related Chinese Patent Application No. 201880040951.8.

Decision to Grant a Patent of the Japanese Patent Office dated Nov. 19, 2021 for related Japanese Patent Application No. 2019-563290.

Grant of Patent of the Korean Patent Office dated Dec. 20, 2021 for related Korean Patent Application No. 10-2019-7033930.

Grant of Patent of the Korean Patent Office dated Oct. 26, 2021 for related Korean Patent Application No. 10-2019-7037287.

Non-Final Office Action of the U.S. Patent Office dated Dec. 24, 2021 for related U.S. Appl. No. 17/021,860.

(56) References Cited

OTHER PUBLICATIONS

Notification of Reason for Refusal of the Korean Patent Office dated Dec. 20, 2021 for related Korean Patent Application No. 10-2020-7007352.
Notice of Allowance of the U.S Patent Office dated Oct. 12, 2021 for related U.S. Appl. No. 16/653,565.
Notification of Reason for Refusal of the Korean Patent Office dated Oct. 21, 2021 for related Korean Patent Application No. 10-2019-7034549.
Decision of Refusal of the Japanese Patent Office dated May 11, 2021 for related Japanese Patent Application No. 2019-563141.
Examiner's Decision of Refusal of the Japanese Patent Office dated Jun. 22, 2021 for related Japanese Patent Application No. 2019-563190.
Notice of Final Office Action of the Korean Patent Office dated May 27, 2021 for related Korean Patent Application No. 10-2019-7037287.
Notice of Reasons for Refusal of the Japanese Patent Office dated Jun. 22, 2021 for related Japanese Patent Application No. 2019-563290.
Notification of Reason for Refusal of the Korean Patent Office dated Jun. 9, 2021 for related Korean Patent Application No. 10-2019-7033930.
Examination Report No. 1 of the Australian Patent Office dated Jul. 23, 2021 for related Australian Patent Application No. 2020260428.
Grant of Patent of the Korean Patent Office dated Aug. 23, 2021 for related Korean Patent Application No. 10-2019-7034862.
Notice of Allowance of the U.S. Patent Office dated Aug. 9, 2021 for related U.S. Appl. No. 16/653,565.
Notice of Allowance of the U.S. Patent Office dated Jul. 23, 2021 for related U.S. Appl. No. 16/653,565.
Notice of Allowance of the U.S. Patent Office dated Sep. 10, 2021 for related U.S. Appl. No. 16/653,565.
Notification to Grant Patent Right for Invention of the Chinese Patent Office dated Sep. 3, 2021 for related Chinese Patent Application No. 201880040951.8.
Office Action of the Canadian Patent Office dated Aug. 17, 2021 for related Canadian Patent Application No. 3060359.
Examination Report No. 1 of the Australian Patent Office dated Jan. 24, 2020 for related Australian Patent Application No. 2018276946.
Examination Report No. 1 of the Australian Patent Office dated Jan. 31, 2020 for related Australian Patent Application No. 2018271773.
Examination Report No. 1 of the Australian Patent Office dated Jul. 13, 2020 for related Australian Patent Application No. 2018278218.
Examination Report No. 1 of the Australian Patent Office dated May 11, 2020 for related Australian Patent Application No. 2018289123.
Examination Report No. 1 of the Australian Patent Office dated Oct. 12, 2020 for related Australian Patent Application No. 2018341716.
Final Office Action of the U.S. Patent Office dated Jan. 7, 2020 for related U.S. Appl. No. 15/785,341.
Final Office Action of the U.S. Patent Office dated Sep. 6, 2019 for related U.S. Appl. No. 15/785,331.
International Search Report and Written Opinion of the PCT Patent Office dated Aug. 9, 2018 for related PCT Patent Application No. PCT/US2018/033056.
International Search Report and Written Opinion of the Searching Authority, dated Aug. 23, 2018, for PCT application No. PCT/US2018/034229.
International Search Report and Written Opinion of the Searching Authority, dated Sep. 13, 2018, for PCT application No. PCT/US2018/034945.
International Search Report and Written Opinion of the Searching Authority, dated Sep. 20, 2018, for PCT application No. PCT/US2018/035900.
International Search Report and Written Opinion of the Searching Authority, dated Sep. 27, 2018, for PCT application No. PCT/US2018/036566.
Non-Final Office Action of the U.S. Patent Office dated Jan. 3, 2020 for related U.S. Appl. No. 15/785,331.

Non-Final Office Action of the U.S. Patent Office dated Mar. 31, 2020 for related U.S. Appl. No. 15/785,291.
Non-Final Office Action of the U.S. Patent Office dated May 28, 2019 for related U.S. Appl. No. 15/785,331.
Non-Final Office Action of the U.S. Patent Office dated Nov. 5, 2018 for related U.S. Appl. No. 15/725,093.
Non-Final Office Action of the U.S. Patent Office dated Sep. 6, 2019 for related U.S. Appl. No. 15/785,341.
Notice of Acceptance of the Australian Patent Office dated Aug. 3, 2020 for related Australian Patent Application No. 2018271773.
Notice of Acceptance of the Australian Patent Office dated Jul. 28, 2020 for related Australian Patent Application No. 2018289123.
Notice of Allowance of the U.S. Patent Office dated Apr. 4, 2018 for related U.S. Appl. No. 15/717,599.
Notice of Allowance of the U.S. Patent Office dated Jul. 15, 2020 for related U.S. Appl. No. 15/785,331.
Notice of Allowance of the U.S. Patent Office dated Jul. 17, 2019 for related U.S. Appl. No. 15/725,093.
Notice of Allowance of the U.S. Patent Office dated Mar. 18, 2019 for related U.S. Appl. No. 15/725,093.
Notice of Allowance of the U.S. Patent Office dated May 26, 2020 for related U.S. Appl. No. 15/785,341.
Notice of Allowance of the U.S. Patent Office dated Sep. 25, 2020 for related U.S. Appl. No. 15/785,291.
Notice of Allowance of the U.S. Patent Office dated Sep. 28, 2020 for related U.S. Appl. No. 15/785,331.
Notice of Allowance of the U.S. Patent Office dated Sep. 9, 2020 for related U.S. Appl. No. 15/785,341.
Notice of Allowance of the U.S Patent Office dated Nov. 12, 2020 for related U.S. Appl. No. 15/785,291.
Notice of Allowance of the U.S Patent Office dated Oct. 30, 2020 for related U.S. Appl. No. 15/785,291.
Notice of Reasons for Refusal of the Japanese Patent Office dated Oct. 27, 2020 for related Japanese Patent Application No. 2019-563141.
Notice of Reasons for Refusal of the Japanese Patent Office dated Oct. 27, 2020 for related Japanese Patent Application No. 2019-563190.
Notice of Reasons for Rejection of the Japanese Patent Office dated Nov. 4, 2020 for related Japanese Patent Application No. 2019-563192.
Supplementary European Search Report of the European Patent Office dated Nov. 19, 2020 for related European Patent Application No. 18806664.1.
Supplementary European Search Report of the European Patent Office dated Nov. 23, 2020 for related European Patent Application No. 18808974.2.
Extended European Search Report [Communication pursuant to Rules 70(2) and 70a (2) EPC] of the European Patent Office dated Dec. 8, 2020 for related Korean Patent Application No. 18806664.1.
Notice of Office Action of the Korean Patent Office dated Feb. 22, 2021 for related Korean Patent Application No. 10-2019-7034862.
Supplementary European Search Report and Search Opinion of the European Patent Office dated Mar. 18, 2021 for related European Patent Application No. 18862162.7.
Notice of Acceptance of the Australian Patent Office dated Nov. 10, 2020 for related Australian Patent Application No. 2018278218.
Notice of Reasons for Refusal of the Japanese Patent Office dated Dec. 1, 2020 for related Japanese Patent Application No. 2019-563290.
Office Action of the Canadian Patent Office dated Dec. 17, 2020 for related Canadian Patent Application No. 3060879.
Supplementary European Search Report and Search Opinion of the European Patent Office dated Dec. 11, 2020 for related European Patent Application No. 18810600.9.
Supplementary European Search Report and Search Opinion of the European Patent Office dated Dec. 14, 2020 for related European Patent Application No. 18820247.7.
Notice of Allowability of the U.S. Patent Office dated Dec. 18, 2020 for related U.S. Appl. No. 15/785,291.
Notice of Allowance of the U.S. Patent Office dated Jan. 11, 2021 for related U.S. Appl. No. 15/785,291.

(56) References Cited

OTHER PUBLICATIONS

Office Action of the Canadian Patent Office dated Dec. 17, 2020 for related Canadian Patent Application No. 3060359.
Office Action of the Canadian Patent Office dated Dec. 18, 2020 for related Canadian Patent Application No. 3060993.
First Office Action and Search Report of the China National Intellectual Property Administration dated Jun. 1, 2022 for related Chinese Patent Application No. 201880033717.2.
First Office Action and Search Report of the China National Intellectual Property Administration dated Jun. 1, 2022 for related Chinese Patent Application No. 201880035692.X.
Notice of Preliminary Rejection of the Korean Patent Office dated Jun. 8, 2021 for related Korean Patent Application No. 10-2020-7007352.
Decision to Grant a Patent of the Japanese Patent Office dated Aug. 24, 2021 for related Japanese Patent Application No. 2019-563192.
Decision to Grant a Patent of the Japanese Patent Office dated Nov. 16, 2021 for related Japanese Patent Application No. 2019-563190.
Final Office Action of the U.S. Patent Office dated Aug. 1, 2022 for related U.S. Appl. No. 17/021,860.
First Office Action of the Chinese Patent Office dated Jun. 20, 2022 for related Chinese Patent Application No. 201880035704.9.
Non-Final Office Action of the U.S. Patent Office dated May 20, 2022 for related U.S. Appl. No. 17/070,822.
Notice of Allowance for Canadian Application No. 3,060,993, dated Oct. 14, 2021, 1 page.
Office Action of the BR Patent Office dated Jul. 21, 2022 for related BR Patent Application No. 112019021760-6.
Office Action of the BR Patent Office dated Sep. 7, 2022 for related BR Patent Application No. 112019022313-4.
Request for the Submission of an Opinion of the Korean Patent Office dated Jun. 8, 2022 for related Korean Patent Application No. 10-2020-7007352.
Search Report of the Chinese Patent Office dated Aug. 26, 2021 for related Chinese Patent Application No. 201880040951.8.
Written Decision on Registration of the Korean Patent Office dated Mar. 21, 2022 for related Korean Patent Application No. 10-2019-7034549.
Office Action of the BR Patent Office dated Sep. 12, 2022 for related BR Patent Application No. 112019022051-8.
Notice of Allowance for U.S. Appl. No. 17/070,822 dated Oct. 12, 2022, 18 pages.
Office Action for Japanese Patent Application No. 2021-176398, dated Oct. 11, 2022, 10 pages (including translation).

* cited by examiner

CART FOR ROBOTIC ARMS AND METHOD AND APPARATUS FOR REGISTERING CART TO SURGICAL TABLE

CROSS-REFERENCE TO RELATED APPLICATIONS

This application is a continuation of U.S. patent application Ser. No. 15/785,331, filed on Oct. 16, 2017, which claims priority to and the benefit of U.S. Provisional Application No. 62/513,327, filed May 31, 2017, entitled "Cart for Robotic Arms and Method and Apparatus for Registering Cart to Surgical Table," the disclosures of which are incorporated by reference herein in their entireties.

BACKGROUND

Embodiments described herein relate to apparatus and methods for a robotic arm cart for transporting, delivering, and securing robotic arms to, for example, a surgical table.

SUMMARY

Apparatus and methods for providing a robotic arm cart for transporting, delivering, and securing robotic arms to a surgical table having a table top on which a patient can be disposed are described herein, and for registering the cart with the surgical table in preparation for transfer of the robotic arm(s). In some embodiments, an apparatus can include a cart for a surgical robotic arm having a coupler releasably coupleable to a coupling site on a surgical table. The cart can include a base and a first engagement feature. The base can be freely movably on a support surface between a first location remote from the surgical table and a second location adjacent the surgical table. The first engagement feature can be configured for engagement with a second engagement feature associated with the surgical table such that, when the first engagement feature and the second engagement feature are engaged, the coupler of the robotic arm is disposed in a position in which the coupler of the robotic arm can be engaged by the coupler of the surgical table.

DETAILED DESCRIPTION

Apparatus and methods for providing a robotic arm cart for transporting, delivering, and securing robotic arms to a surgical table having a table top on which a patient can be disposed are described herein. In some embodiments, an apparatus can include a cart for a surgical robotic arm having a coupler releasably coupleable to a coupling site on a surgical table. The cart can include a base and a first engagement feature. The base can be freely movably on a support surface between a first location remote from the surgical table and a second location adjacent the surgical table. The first engagement feature can be configured for engagement with a second engagement feature associated with the surgical table such that, when the first engagement feature and the second engagement feature are engaged, the coupler of the robotic arm is disposed in a position in which the coupler of the robotic arm can be engaged by the coupler of the surgical table.

Figure 1A:
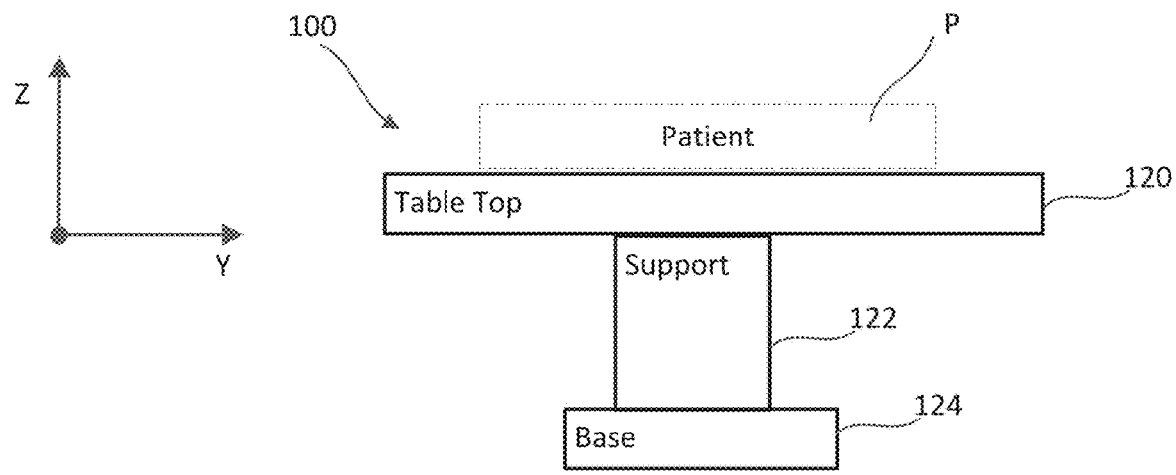
FIGS. 1A and 1B are a schematic side view and a schematic top view, respectively, of a surgical table, according to an embodiment.
Figure 1B:
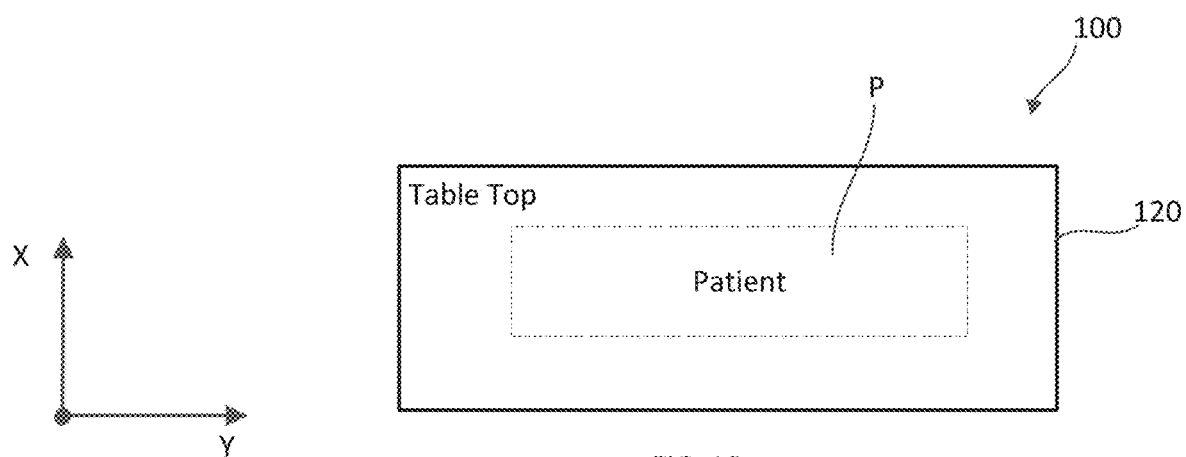

As shown schematically in FIGS. 1A-1B, a surgical table 100 includes a table top 120, a table support 122, and a table base 124. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a pedestal) may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axes. The table top 120 may also include multiple sections that are movable relative to each other along/about any suitable axes, e.g., separate sections for each of the torso, one or both legs, and/or one or both arms, and a head support section.

Movement of the table top 120 and/or its constituent sections may be performed manually, driven by motors, controlled remotely, or achieved through any other suitable means. The support 122 for the table top 120 may be mounted to the base 124, which can be fixed to the floor of the operating room, or can be movable relative to the floor, e.g., by use of wheels on the base 124. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the base 124. This also can allow robotic arms (e.g., arms 130 discussed below) coupled to the table 100 to reach a desired treatment target on a patient P disposed on the table top 120.

In a robotically-assisted surgical procedure, one or more robotic arms 130 (shown schematically in FIGS. 1C and 1D) can be disposed in a desired operative position relative to a patient disposed on the table top 120 of the surgical table 100 (also referred to herein as "table"). The robotic arm(s) 130 can be used to perform a surgical procedure on a patient disposed on the surgical table 100. In particular, the distal end of each robotic arm 130 can be disposed in a desired operative position so that a medical instrument coupled to the distal end of the robotic arm 130 can perform a desired function.

Figure 1C:
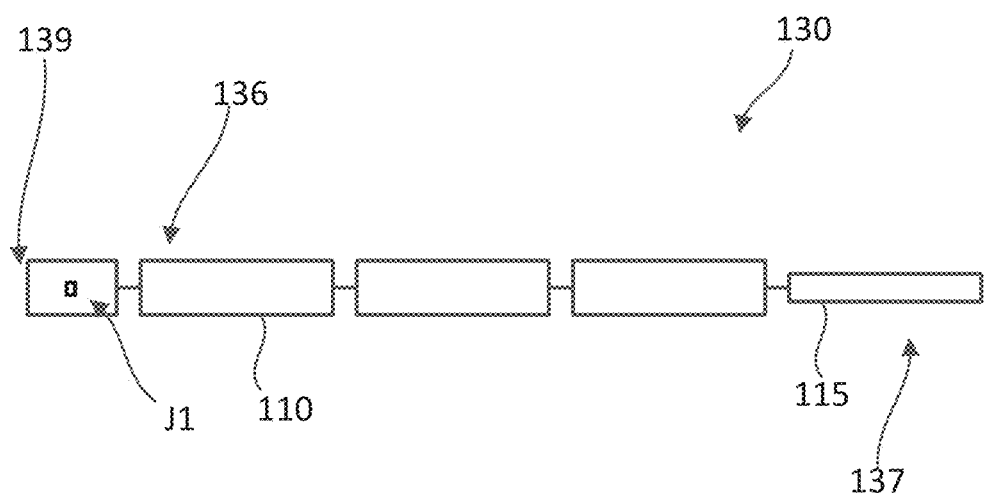
FIG. 1C is a schematic side view of a robotic arm, according to an embodiment, shown in an extended or use configuration.
Figure 1D:
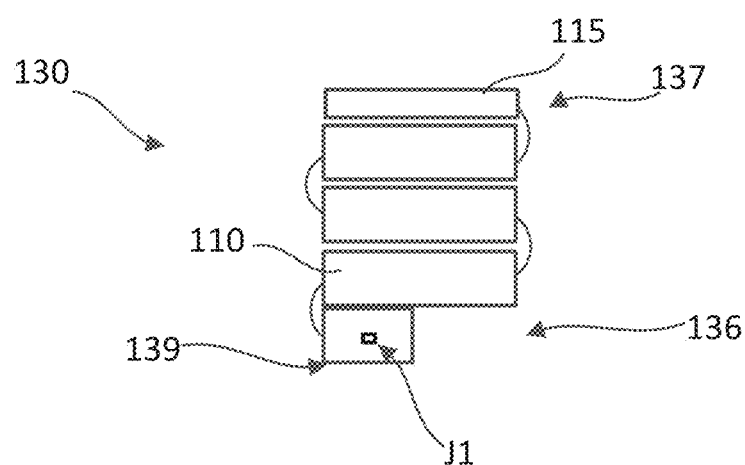
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include a coupling portion to allow the robotic arm 130 to be coupled to the table 100. The robotic arm 130 can include two or more link members or segments 110 coupled together at joints that can provide for translation along and/or rotation about one or more of the X, Y and/or Z axes (shown, for example, in FIGS. 1A and 1B). The coupling portion of the robotic arm 130 can include a coupling mechanism 139. The coupling mechanism 139 can be disposed at the mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling mechanism 139 and/or the coupling portion or can be disposed on a link or segment 110 of the robotic arm 130 that is coupled to the coupling portion. The target joint J1 can provide a pivot joint to allow a distal segment of the robotic arm 130 to pivot relative to the table 100. The robotic arm 130 can be moved between various extended configurations for use during a surgical procedure, as shown in FIG. 1C, and various folded or collapsed configurations for storage when not in use, as shown in FIG. 1D.

FIGS. 2A-13C illustrate various embodiments describing apparatus and methods for transporting, delivering, and securing a robotic arm to a surgical table. As described above and in accordance with various embodiments disclosed in more detail below, a robotic arm for use in performing a surgical procedure may be releasably coupled to a surgical table. In some embodiments, robotic arms can be coupled at a fixed location on the table or can be coupled such that the robotic arms can be movable to multiple locations relative to the table top. For example, as shown schematically in FIG. 2A, robotic arms 230 can be coupled to a table top 220 of a surgical table 200. The surgical table 200 can be the same or similar in structure and function to the surgical table 100 described above. For example, the table top 220 has an upper surface on which a patient P can be disposed during a surgical procedure. In some embodiments, the robotic arms 230 can be permanently or releasably coupled, in a fixed or movable location, to an arm adapter (also referred to as an "arm support") that is coupled to or separate from the surgical table. For example, as shown schematically in FIG. 2B, an arm adapter 246 can be coupled to or separate from but engageable with or couplable to the table top 220. The robotic arms 230 can be coupled to the arm adapter 246.

Figure 2A:
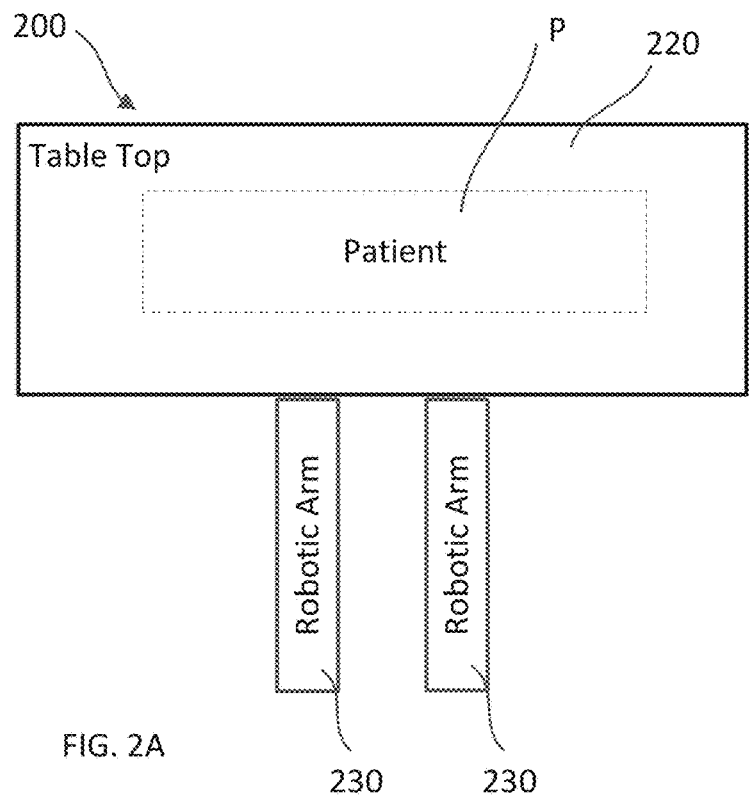
FIG. 2A is a schematic top view of a surgical table with robotic arms coupled thereto, according to an embodiment.
Figure 2B:
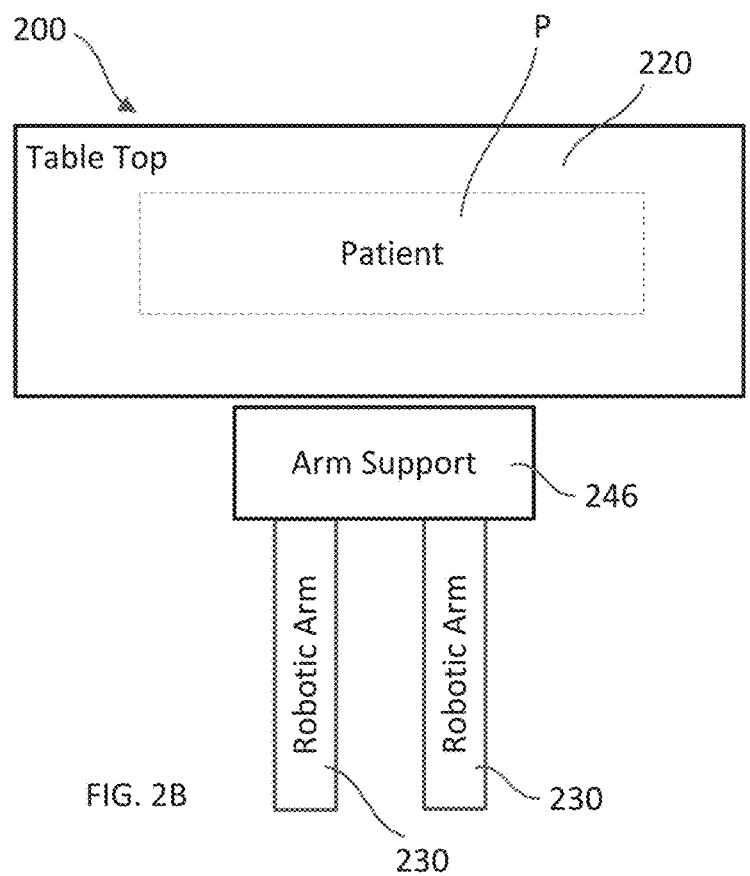
FIG. 2B is a schematic top view of a surgical table with robotic arms and an arm adapter coupled thereto, according to an embodiment.

In preparation for a robotically-assisted surgical procedure in which one or more robotic arms are releasably coupled to the surgical table and/or to an arm adapter, as described with respect to FIGS. 2A and 2B, each robotic arm may be delivered and connected to the surgical table and/or the arm adapter via an arm cart. As shown schematically in FIG. 3, an arm cart 350 can be configured to support one or more robotic arms 330. Specifically, the arm cart 350 includes a first robotic arm 330A and can include an optional second robotic arm 330B. Although two robotic arms 330 are shown, the arm cart 350 can be configured to contain, transport, and/or deliver any suitable number of robotic arms 330, such as, for example, one robotic arm, three robotic arms, or four robotic arms.

The arm cart 350 can support the first robotic arm 330A (and the optional second robotic arm 330B) in a variety of configurations. In some embodiments, the arm cart 350 can support the robotic arm 330A such that the center of gravity of the robotic arm 330A is below one or more support structure locations (e.g., cradles) of the arm cart 350 such that the stability of the robotic arm 330A and the arm cart 350 is increased. In some embodiments, the arm cart 350 can support the robotic arm 330A such that the arm cart 350 bears most or all of the weight of the robotic arm 330A and a coupling mechanism (not shown) of the robotic arm 330A can be manually manipulated by a user without the user bearing the most or all of the weight of the robotic arm. For example, the robotic arm 330A can be suspended from a structure of the arm cart 350 or rested on a structure of the arm cart 350. In some embodiments, the arm cart 350 can be configured to secure the robotic arm 330 to the arm cart 350.

The arm cart 330 can be configured for movement such as, for example, by including wheels. The arm cart 350 can be configured to protect the robotic arm 330A from potential impact with the surrounding of the arm cart 350 during, for example, transport or storage. In some embodiments, the arm cart 350 can be configured to move the robotic arm 330 between one or more positions and/or one or more orientations, including, for example, a folded storage or transport position and a deployed or coupling position.

The arm cart 350 can include an arm container 352 and a base 354. The arm container 352 is configured to support, protect, and promote sterility for one or more robotic arms 330 (e.g., the first robotic arm 330A and the optional second robotic arm 330B) during transportation of the robotic arms 330, for example, from a storage area to the operating area, and during transfer of the one or more robotic arms 330 from the arm cart 350 to a surgical table (e.g., the surgical table 100 and/or the surgical table 200) for use during the surgical procedure. While the one or more robotic arms 330 are stored and/or transported by the arm cart 350, the one or more robotic arms 330 can be mostly, substantially completely, or completely maintained within the footprint of the arm cart 350 such that the one or more robotic arms 330 will be less likely to be accidentally bumped or damaged. In some embodiments, the arm container 352 can be structured as a vertically-extending protection frame that, in combination with the base 354, defines a space for storing the one or more robotic arms 330. In some embodiments, when the one or more robotic arms 330 are stored within the arm cart 350, the robotic arms can be maintained within the perimeter of the base 354, but may extend beyond the perimeter of the arm container 352.

The arm container 352 can be further configured to facilitate safe, efficient, sterile, and repeatable transfer of the one or more robotic arms 330 to the surgical table and/or an arm adapter. In some embodiments, transfer of the one or more robotic arms 330 from the arm cart 350 to the surgical table can be performed manually.

The base 354 can be configured to support the arm container 352 and provide transportation of the arm cart 350 to the surgical area. The base 354 can include any suitable means for movement of the arm cart 350 relative to the floor. For example, the base 354 can include wheels such that a medical provider can push/pull the arm cart to/from the operating area.

The arm cart 350 can include features that assist in aligning the one or more robotic arms 330 for transfer to the surgical table along the X, Y, and/or Z axes and/or rotationally about the X, Y, and/or Z axes. For example, as described above, the base 354 can include any suitable means for movement of the arm cart 350 such that the arm cart 350 can be moved along the X axis and/or the Y axis relative to the surgical table. Additionally, the arm cart 350 can include any suitable means for adjusting the height of the arm cart 350 and/or the one or more robotic arms 330 such that the height of the one or more robotic arms 330 can be adjusted relative to the surgical table. Thus, the arm cart 350 can move the one or more robotic arms 330 along the X, Y, and/or Z axes and/or rotationally about the X, Y, and/or Z axes such that a coupling portion of at least one of the one or more robotic arms 330 can be aligned for engagement with a mating coupling portion on a table or a table adapter.

In some embodiments, the arm cart 350 houses the one or more robotic arms 330 such that a line of sight can be maintained from the operator of the arm cart 350 to the portion of the surgical table to which the one or more robotic arms 330 are to be transferred during the approach of the arm cart 350 to the surgical table and the transfer of the one or more robotic arms 330 to the surgical table.

Figure 3:
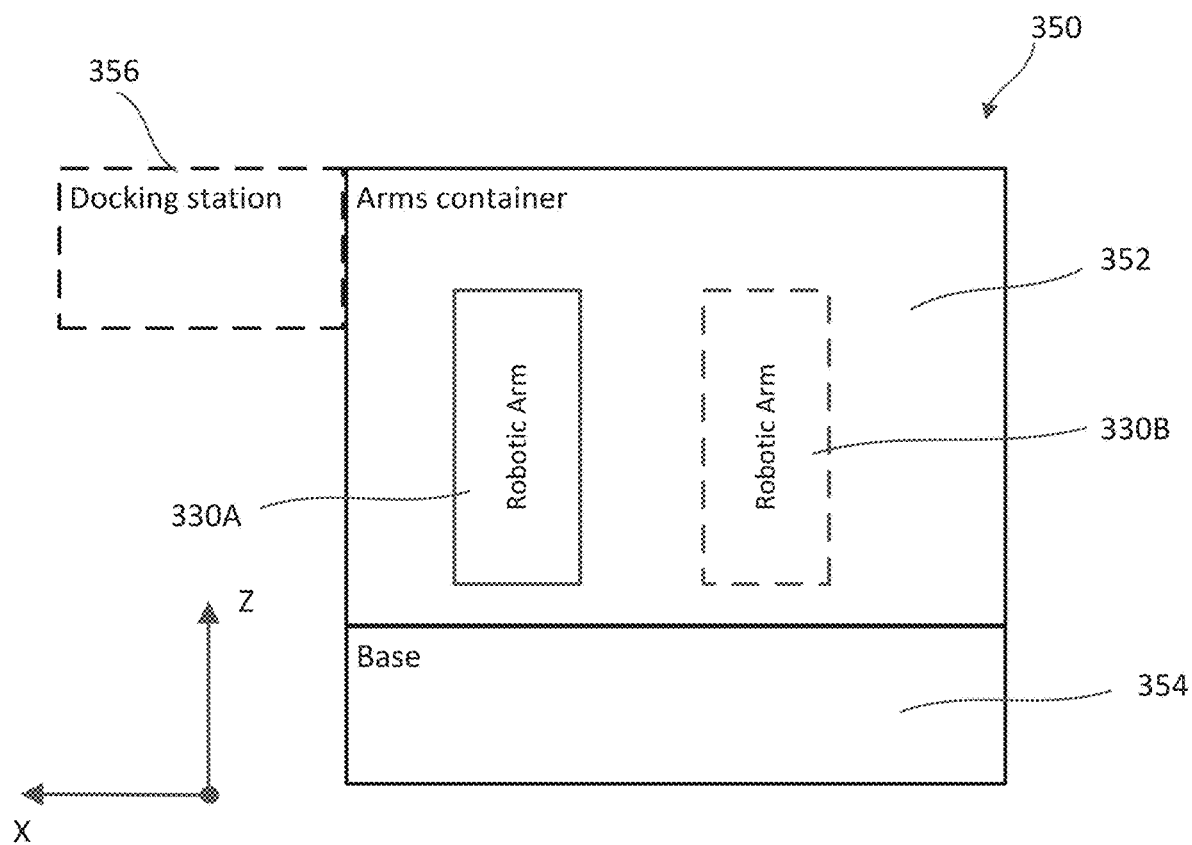
FIG. 3 is a schematic illustration of an arm cart according to an embodiment.

As shown in FIG. 3, the arm cart 350 may optionally include one or more docking stations 356 configured to be releasably attached to the surgical table and/or an arms support connected to the surgical table. In this manner, the arm cart 350 can be fixed to the surgical table and/or arms support during transfer of one or more robotic arms 330 from the arm cart 350, and then the arm cart 350 can be removed from the operating area.

The one or more robotic arms 330 can be docked and/or mounted to the surgical table 300 using a variety of different types of coupling and/or mounting methods and mechanisms. The arm cart 350 can employ corresponding coupling methods and mechanisms to provide efficient transfer of the robotic arms 330 from the arm cart 350 to any suitable location on the surgical table 300 and/or an arms support associated with the surgical table 300. In this manner, the arm cart 350 and the surgical table 300 can include a common interface such that the robotic arms 330 can be efficiently and repeatedly coupled to and/or removed from the surgical table 300 and the arm cart 350.

In some embodiments, a first coupling member associated with the robotic arm can be configured to engage with a second coupling member associated with the surgical table.

Figure 4:
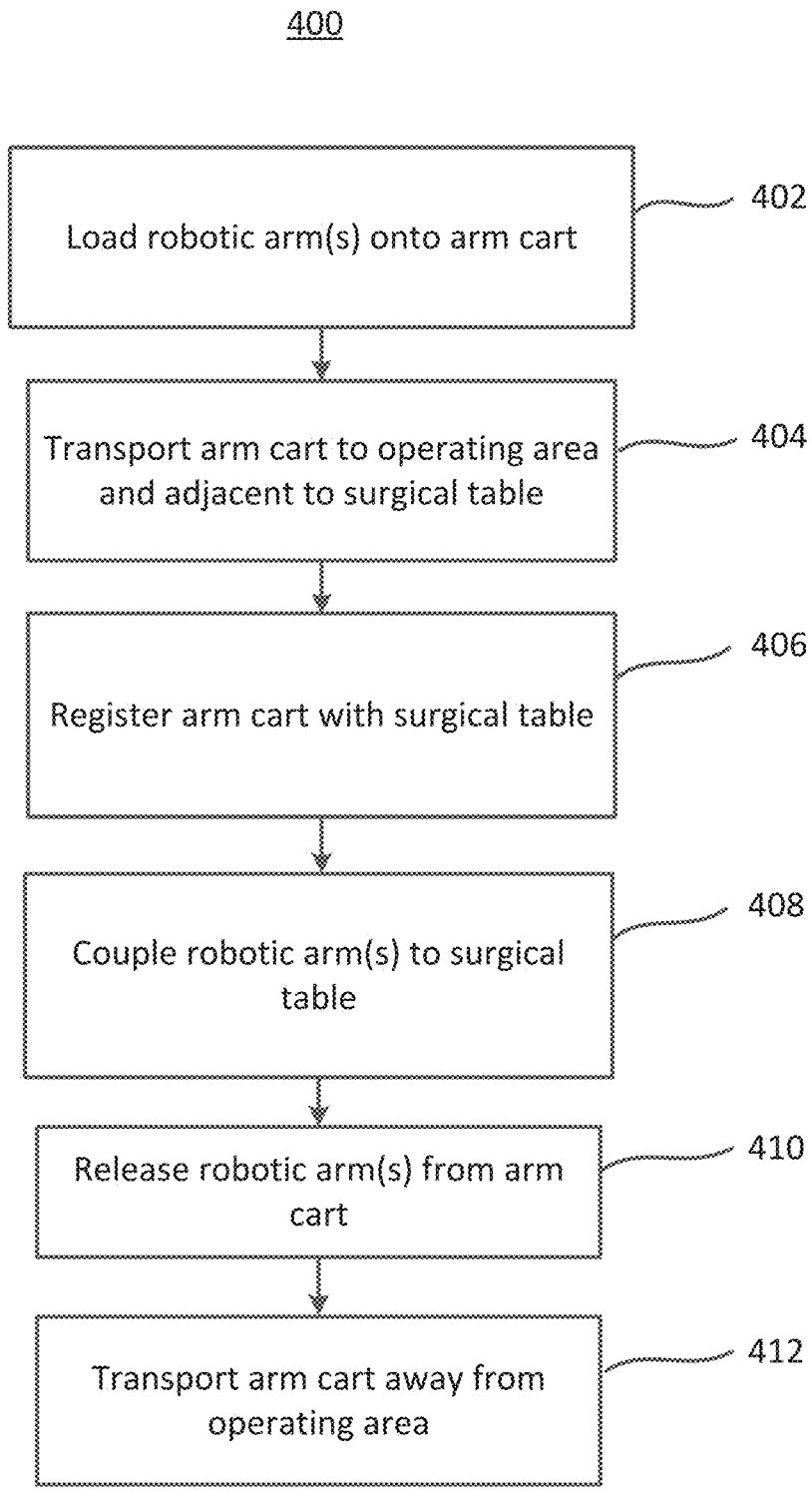
FIG. 4 is a flowchart of a method of using an arm cart to transport robotic arms to a surgical table and to register the arm cart with the table in preparation for transferring the arms from the cart to the surgical table, according to an embodiment.

FIG. 4 is a flow chart of a method 400 of using an arm cart to transport robotic arms to a surgical table and to register the arm cart with the table in preparation for transferring the arms from the cart to the surgical table. The arm cart of the method 400 can be, for example, any of the arm carts described herein. The method 400 includes loading one or more robotic arms onto an arm cart at 402. For example, one or more robotic arms can be releasably coupled to an arm support of the arm cart. The arm support can be coupled to a base of the arm cart to support the one or more robotic arms above the base. The base can be freely movable on a support surface. The arm cart is then transported to an operating area and adjacent to a surgical table, at 404. The arm cart is registered with the surgical table via, for example, mechanical or electronic registration, at 406. In some embodiments, registration of the arm cart with the surgical table results in at least one of the one or more robotic arms being positioned such that an arm portion of a coupler disposed on the at least one of the one or more robotic arms is disposed in operative relationship (i.e., registered) with a table portion of a coupler disposed on the surgical table. In some embodiments, registration of the arm cart with the surgical table results in at least one of the one or more robotic arms being positioned such that the one or more robotic arms can move or be moved relative to the arm cart and the surgical table into a configuration and/or position in which an arm portion of a coupler disposed on the at least one of the one or more robotic arms is in an operative relationship with a table portion of a coupler disposed on the surgical table. The one or more robotic arms are coupled to the surgical table, at 408. For example, in some embodiments, the arm portion of the coupler can be releasably coupled to the table portion of the coupler. The one or more robotic arms are released from the arm cart, at 410. The arm cart is transported away from the operating area, at 412.

In some embodiments, if a second robotic arm has been loaded onto the arm cart, the arm cart can couple a first robotic arm to the surgical table, release the first robotic arm from the arm cart, and then be transported to a location proximate another portion of the surgical table and registered with the surgical table at a second site. If not yet disposed in proper alignment with the surgical table, an arm portion of a second coupler disposed on the second robotic arm can be disposed in operative relationship (i.e., registered) with a table portion of a second coupler disposed on the surgical table. The second robotic arm can then be coupled to the surgical table via, for example, the arm portion of the second coupler being releasably coupled to the table portion of the second coupler. The second robotic arm can be released from the arm cart and the arm cart can be transported away from the operating area.

In some embodiments, an arm cart can move such that a coupling member associated with a robotic arm supported by and/or within the arm cart can be presented at a suitable location for engagement with a complementary coupling member associated with a table. For example, the arm cart can be adjusted to various height settings such that the robotic arm can cooperate with various surgical tables and/or various coupling portions of a surgical table at varying heights. For example, in some embodiments, the arm cart can be moved into position relative to the surgical table such that the coupling member of the robotic arm is aligned with a coupling member associated with the surgical table with respect to the X axis and/or Y axis. The arm cart can then perform a first macro phase of height adjustment in which the robotic arm cart is set to a high, medium, or low height range. Then, in a second micro phase of height adjustment, the arm cart can move the coupling member of the robotic arm cart up or down along the Z axis into engagement with the complementary coupling member of the surgical table. In some embodiments, the arm cart can be registered mechanically or electronically with the surgical table such that the arm cart is properly positioned for a coupling member of the robotic arm to be coupled or to transition into a configuration and/or position to be coupled with the surgical table.

Figure 5A:
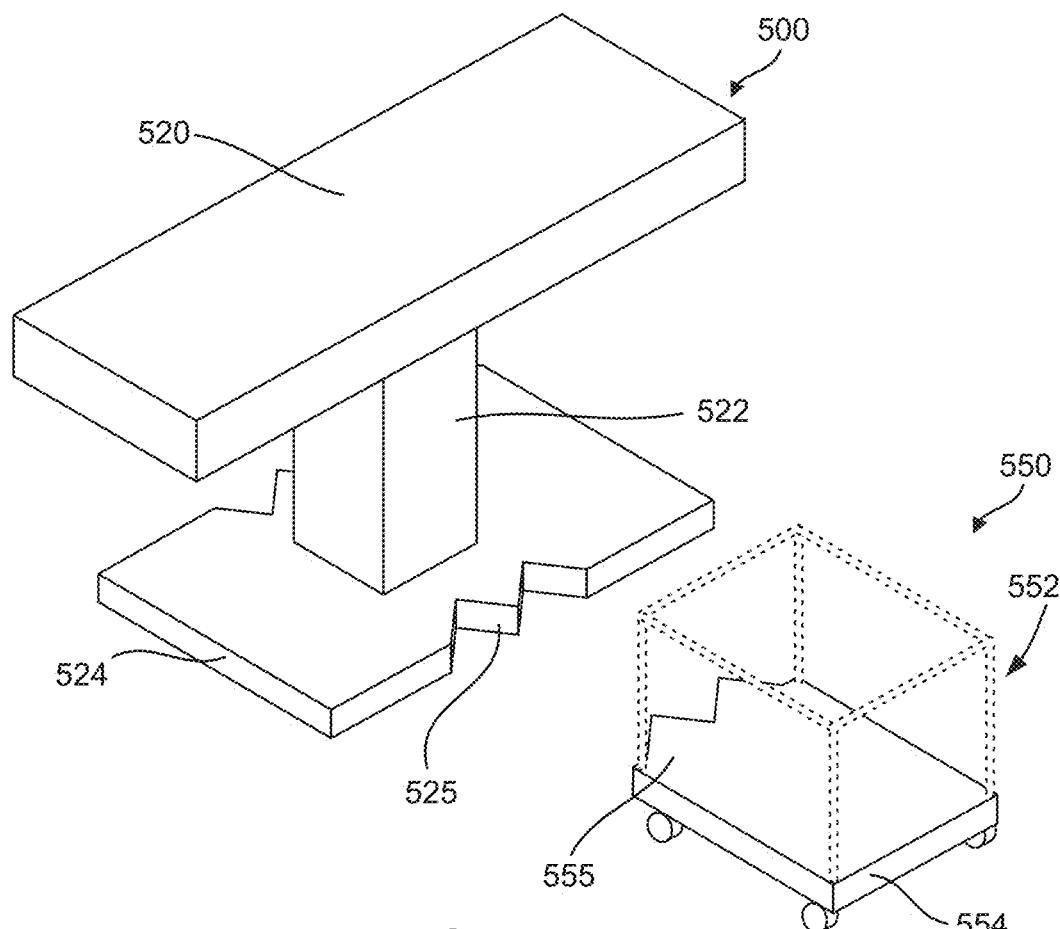
FIG. 5A is a schematic illustration of mechanical registration of an arm cart by interaction of an arm cart base and a table base, according to an embodiment.

FIG. 5A is an illustration of a perspective view of an arm cart 550 and a surgical table 500 in a disengaged configuration. The arm cart 550 can be the same or similar in structure and/or function to any of the arm carts described herein (e.g., arm cart 350). For example, the arm cart 550 can include an arm container 552 (shown in phantom) and a base 554. The arm container 552 is configured to support, protect, and promote sterility for one or more robotic arms (not shown) during transportation of the one or more robotic arms, for example, from a storage area to the operating area, and during transfer of the one or more robotic arms from the arm cart 550 to the surgical table 500 for use during a surgical procedure. The arm container 552 is further configured to facilitate safe, efficient, sterile, and repeatable transfer of the one or more robotic arms to the surgical table 500. Transfer of the robotic arms 530 from the arm cart 550 to the surgical table 500 may be performed manually, driven by motors, controlled remotely, or achieved through any other suitable means. The surgical table 500 can be the same or similar to any of the surgical tables described herein (e.g., the surgical table 100). For example, the surgical table 500 includes a table top 520, a support 522, and a base 524. A patient (not shown) can be disposed on the table top 520.

The arm cart 550 and the surgical table 500 can each include complementary mating features such that the arm cart 550 can register and engage with the surgical table 500. For example, as shown in FIG. 6A, the base 554 of the arm cart 550 can include a first mating feature 555 and the table base 524 of the surgical table 500 can include a second mating feature 525. The first mating feature 555 can have any suitable shape, such as including triangular or angled lead-ins, as shown in FIG. 6A. The second mating feature 525 can have any suitable shape configured to receive the first mating feature 555, such as including complementary triangular or angled cut-outs. The first mating feature 555 and the second mating feature 525 can be engaged to achieve proper registration (e.g., along and/or about the X, Y, and/or Z axes) between the arm cart 550 and the surgical table 500.

In some embodiments, the first mating feature 555 of the arm cart 550 can protrude from the arm container 552 sufficiently such that the first mating feature 555 can serve as an impact resistor and/or dampener. For example, the first mating feature 555 can extend beyond the outer profile of the arm container 552 farther than a coupling member of a robotic arm supported by the arm cart 550 such that the if the arm cart 550 impacts an obstacle (e.g., a wall or door frame), the force from the impact will be dissipated by the first mating feature 555. Thus, contact and damage to the robotic arm and/or the arm cart 550 can be prevented.

Although the first mating feature 555 is shown as being shaped as two triangular protrusions and the second mating feature 525 is shown as being shaped as two triangular cut outs in FIG. 5A, the first mating feature 555 and the second mating feature 525 can be any suitable shape. For example, the first mating feature 555 can be shaped as a single triangular protrusion and the second mating feature 525 can be shaped as a single triangular cut out. In some embodiments, the first mating feature 555 and the second mating feature 525 can include complementary shapes that are curved, rectangular, or any other suitable shape or combination of shapes.

Although shown as being located on the base 554 of the arm cart 550 and the table base 524 of the surgical table 500, respectively, the first mating feature 555 and the second mating feature 525 can be disposed in any suitable location on the arm cart 550 and/or the surgical table 500 such that engagement of the first mating feature 555 and the second mating feature 525 corresponds to proper registration between the arm cart 550 and the surgical table 500 for robotic arm transfer, e.g. in the X-Y plane. For example, the first mating feature 555 can be disposed on the arm container 552 and the second mating feature 525 can be disposed on the table support 522 or the table top 520 at a similar height to the first mating feature 555.

In some embodiments, the first mating feature 555 and/or the second mating feature 525 can include magnets and/or sensors to assist in alignment and/or engagement between the arm cart 550 and the table 500. For example, the first mating feature 555 and/or the second mating feature 525 can include Hall effect sensors, capacitance sensors, buttons, and or other sensors capable of detecting the presence of the arm cart 550 near or adjacent to the table 500.

In use, the arm cart 550 can be moved (e.g., pushed) toward the second mating feature 525 of the surgical table 500. When the arm cart 550 is near the surgical table 500, the first mating feature 555 can be inserted into engagement with the second mating feature 525 via, for example, maneuvering the position of the arm cart 550. In some embodiments, the shape and size of each of the first mating feature 555 and the second mating feature 525 can be sufficiently complementary and unique such that the arm cart 550 can be guided into a particular position relative to the surgical table 500. For example, the first mating feature 555 and the second mating feature 525 can be shaped and sized such that, once the first mating feature 555 is fully engaged with the second mating feature 525, a coupling member associated with a robotic arm supported by the arm cart 550 is aligned and/or registered with a complementary coupling member associated with the surgical table 500 to facilitate the transfer of the robotic arm to the surgical table 500.

Figure 5B:
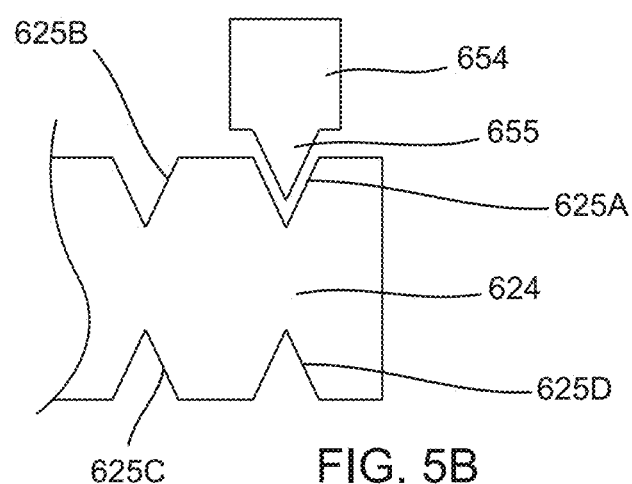
FIG. 5B is a schematic illustration of mechanical registration of an arm cart by interaction of an arm cart base and a table base, according to an embodiment.

In some embodiments, a surgical table can include multiple distinct mating features at discrete locations around the perimeter of the surgical table. For example, FIG. 5B is a top view of a table base 624 and an arm cart base 654. The table base 624 can be the same or similar in structure and/or function to any of the table bases described herein, such as the table base 524 described with respect to FIG. 5A. The arm cart base 654 can be the same or similar in structure and/or function to any of the arm cart bases described herein, such as the base 554 described with respect to FIG. 5A. The table base 624 can include a number of mating features 625, such as a first table mating feature 625A, a second table mating feature 625B, a third table mating feature 625C, and a fourth table mating feature 625D. In some embodiments, each of the mating features 625 of the table base 624 can be associated with a robotic arm engagement location on a table top associated with the table base 624. The arm cat base 654 can include an arm cart mating feature 655. The arm cart mating feature 655 can be shaped and sized such that the arm cart mating feature 655 is configured to engage with the first table mating feature 625A, the second table mating feature 625B, the third table mating feature 625C, and/or the fourth table mating feature 625D. In some embodiments, the arm cart mating feature 655 and the mating features of the table base 624 can be shaped and sized such that the arm cart mating feature 655 is complementarily shaped with and/or configured to engage with any of the mating features 625 (e.g., the first table mating feature 625A, the second table mating feature 625B, the third table mating feature 625C, and the fourth table mating feature 625D) of the table base 624. In some embodiments, the arm cart mating feature 655 and the mating features 625 of the table base 624 can be shaped and sized such that the arm cart mating feature 655 is configured to engage with only one or only some of the mating features 625 of the table base 624. As shown in FIG. 5B, the arm cart mating feature 655 can be triangularly-shaped and the table mating features can include complementary triangularly-shaped cut outs. Although four table mating features 625 are shown, the table base 624 can include any suitable number of table mating features for alignment of an arm cart including the arm cart base 654 with any suitable number of positions of the surgical table including the table base 624.

Figure 6:
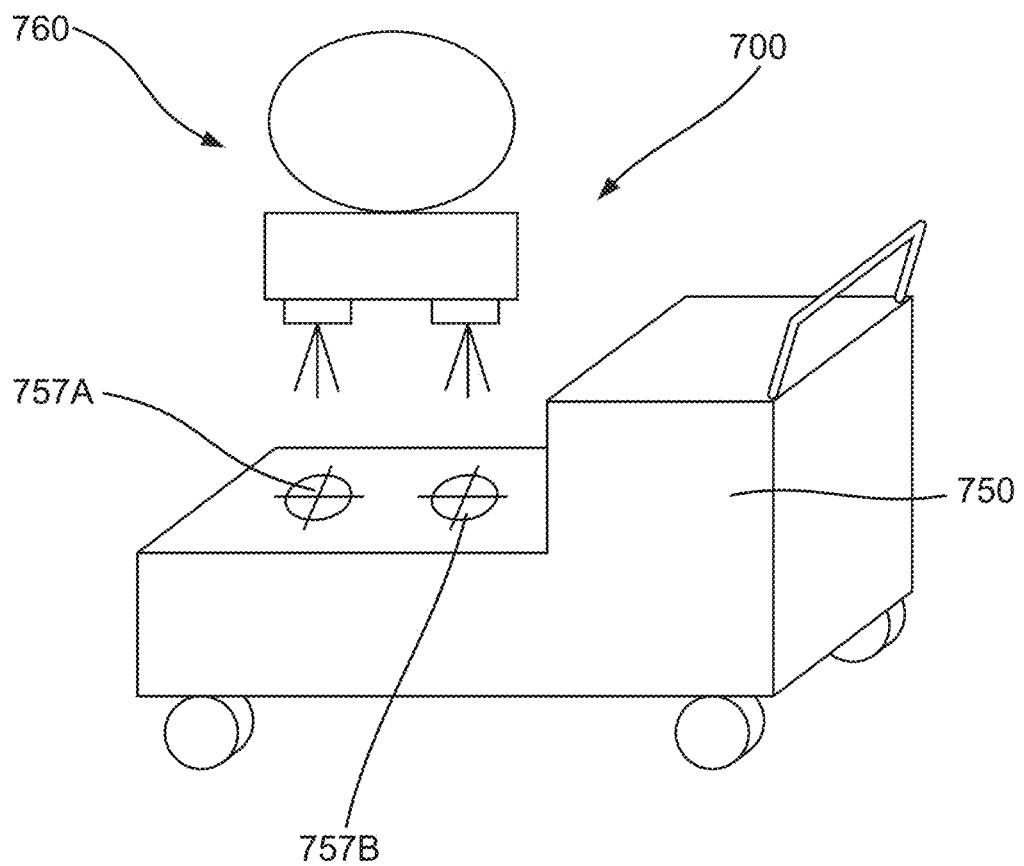
FIG. 6 is a schematic illustration of an optical targeting system, according to an embodiment.

In some embodiments, an optical targeting system can be used to improve the speed and accuracy of registration between an arm cart and a surgical table prior to and during transfer of one or more robotic arms from the arm cart to the surgical table. FIG. 6 is a schematic illustration of an optical targeting system 700 including an arm cart 750 and a light beacon assembly 760. The arm cart 750 can be the same or similar in structure and/or function to any of the arm carts described herein. The arm cart 750 can include one or more targets 757 (e.g., a first target 757A and a second target 757B). The one or more targets 757 can be, for example, crosshair markings on an upper surface of the arm cart 750. The light beacon assembly 760 can be coupled to a surgical table (not shown) or can be positioned in a nearby location and stationary relative to the surgical table. The light beacon assembly 760 can include a light emitter configured to project one or more light beams. The light emitter can project the one or more light beams toward the location where the one or more targets 757 on the arm cart 750 will be located when the arm cart 750 is properly aligned with the surgical table for transfer of one or more robotic arms from the arm cart 750 to the surgical table.

When the arm cart 750 is moved into proper alignment with the light beam (and, therefore, proper alignment with the surgical table), the one or more light beams can be centered on the one or more targets 757. In some embodiments, the centering of the one or more light beams on the one or more targets can be observable by a user such that the user can manually initiate transfer of the one or more robotic arms in response to observing the proper alignment of the one or more light beams with the one or more targets. In some embodiments, the arm cart 750, the light beacon assembly 760, and/or the surgical table can include a sensor (not shown) and/or receptor (not shown) configured to recognize when the one or more light beams are in proper alignment with the one or more targets 757. The sensor can indicate to a user that the arm cart 750 is properly positioned and/or send a signal to initiate automatic transfer of the one or more robotic arm upon proper positioning of the arm cart 750. In some embodiments, the light beacon assembly 760 can project a crosshair or other locating mark such that the crosshair or other locating mark can be aligned with one of the one or more targets 757 of the arm cart 750. Such embodiments can help to eliminate positioning error and reduce the need for a specially-skilled operator to align the arm cart 750 and the surgical table for transfer of the one or more robotic arms.

Figure 7A:
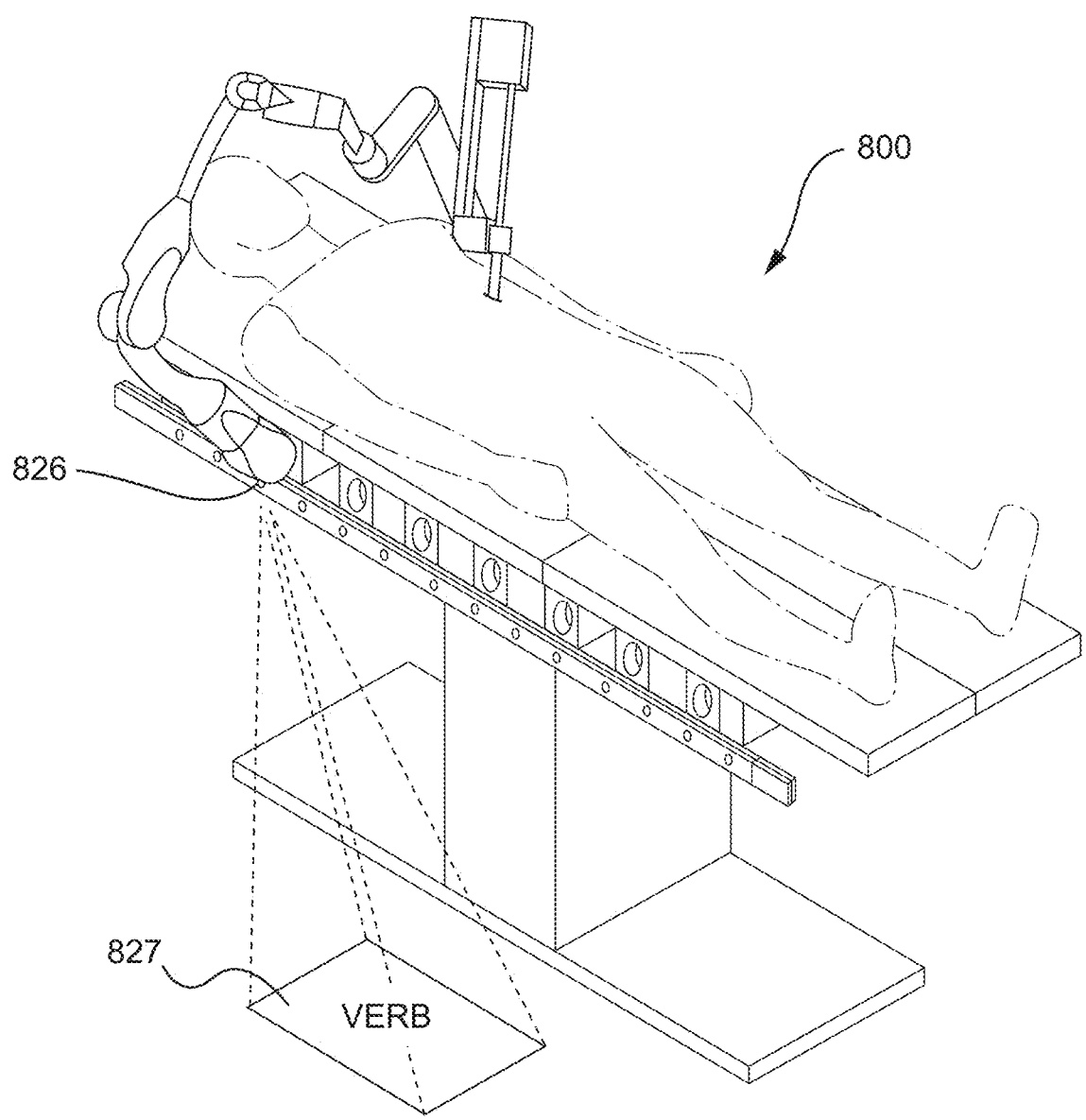
FIG. 7A is a schematic illustration of a surgical table having a projector, according to an embodiment.

In some embodiments, a surgical table can be configured to project an image onto a floor to assist in alignment of an arm cart for transfer of one or more robotic arms. For example, FIG. 7A is a perspective view of a surgical table 800 having a projector 826. The projector 826 can project a temporary floor marking 827 onto the floor. The temporary floor marking 827 can be, for example, a box-shaped target. The temporary floor marking 827 can include an image and/or additional guiding features. Although shown as a rectangular-shaped box, in some embodiments the temporary floor marking 827 can be any suitable shape, such as a circle or crosshairs.

Figure 7B:
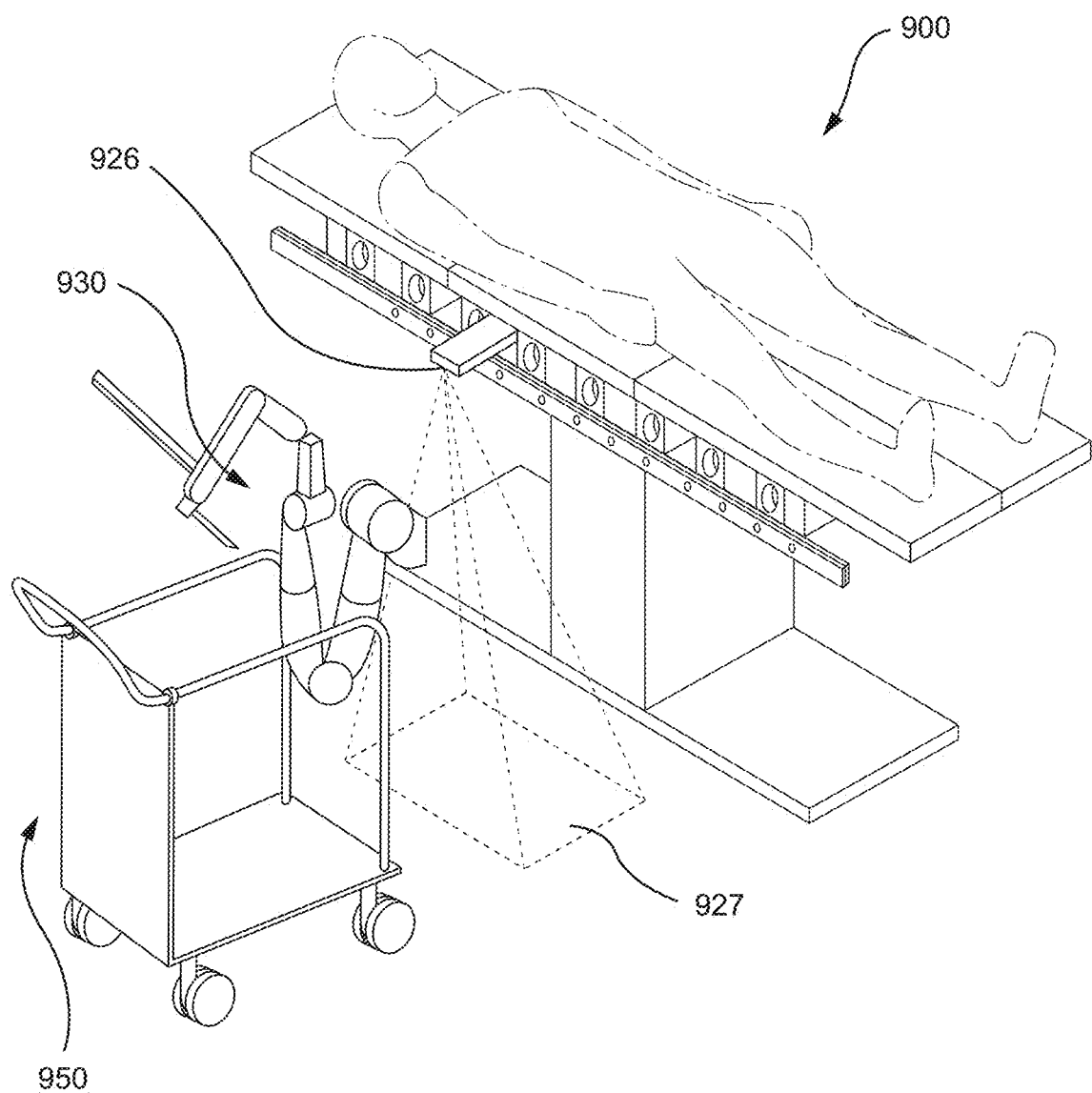
FIG. 7B is an illustration of a surgical table having a projector and an arm cart supporting a robotic arm, according to an embodiment.

FIG. 7B is a perspective view of a surgical table 900 having a projector 926 and an arm cart 950 supporting a robotic arm 930. The surgical table 900 and the projector 926 can be the same or similar in structure and/or function to the surgical table 800 and the projector 826 described above with reference to FIG. 7A. For example, the projector 926 can project a temporary floor marking 927 on a floor near the surgical table 900. In use, the arm cart 950 can be moved relative to the temporary floor marking 927. In some embodiments, the temporary floor marking 927 can provide a "landing zone" such that a user can use the temporary floor marking 927 as a guide and align the arm cart 950 with the temporary floor marking 927. Upon the user's visual confirmation that the arm cart 950 is properly aligned with the temporary floor marking 927, the user can initiate the process for transferring the robotic arm 930 from the arm cart 950 to the surgical table 900. For example, in some embodiments, the user can initiate the transfer of the robotic arm 930 using a graphic user interface. In some embodiments, the arm cart 950 and/or the surgical table 900 can include one or more sensors (not shown) configured to sense when the arm cart 950 is correctly positioned relative to the temporary floor marking 927 (and therefore the surgical table 900) for transfer of the robotic arm 930 to the surgical table 900. In some embodiments, the one or more sensors can signal the projector 926 to change the temporary floor marking 927 to indicate proper positioning of the arm cart 950, such as, for example, by changing the color of the temporary floor marking 927. In some embodiments, the indication of proper positioning of the arm cart 950 relative to the table 900 can initiate the one or more robotic arms to automatically self-navigate and engage with the table 900, as described below. The projector 926 can be configured to change the color of the temporary floor marking 927 a second time (e.g., revert to the original color) if the arm cart 950 is moved out of proper alignment with the temporary floor marking 927.

Figure 8A:
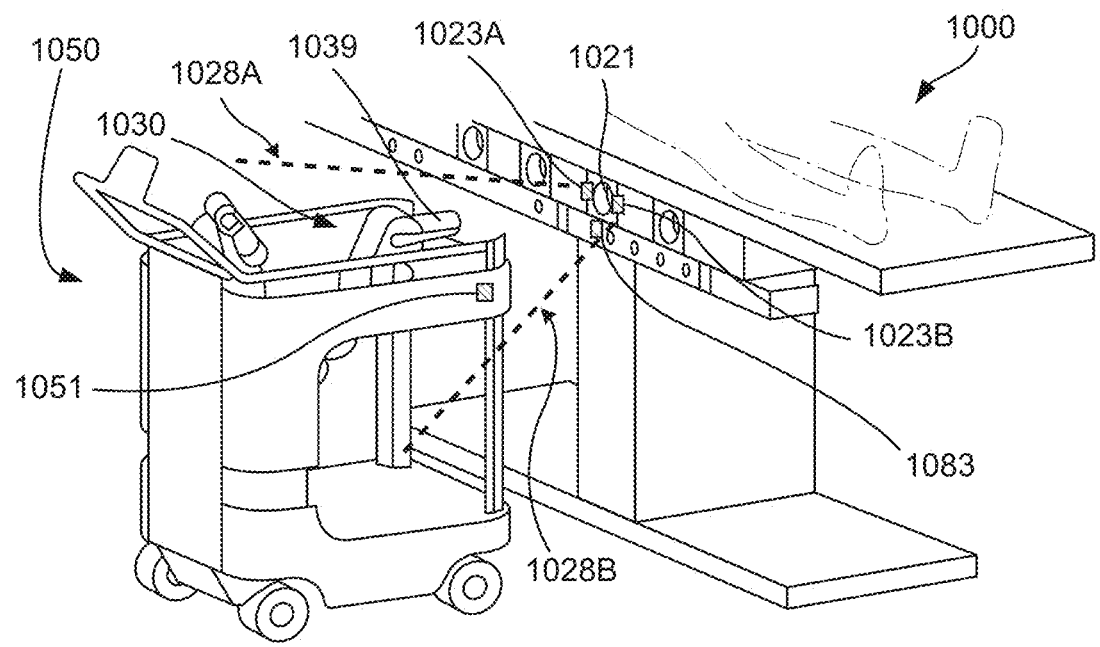
FIGS. 8A and 8B are schematic illustrations of a surgical table having infrared and motion sensors for alignment of an arm cart to a table, according to an embodiment.

In some embodiments, an arm cart can be configured to be automatically guided into proper alignment with the surgical table. FIG. 8A is a perspective view of a surgical table 1000, an arm cart 1050, and a robotic arm 1030. The surgical table 1000, the arm cart 1050, and the robotic arm 1030 can be the same or similar in structure and/or function to any of the surgical tables, arm carts, and robotic arms described herein, respectively. The surgical table 1000 can include an attachment interface 1021. The surgical table 1000 can also include light emitters 1023 (e.g., a first light emitter 1023A and a second light emitter 1023B). The first light emitter 1023A and the second light emitter 1023B each emit light signals to create light wall barriers 1028A and 1028B, respectively. The light wall barriers 1028A and 1028B can be angled such that the light wall barriers 1028A and 1028B diverge away from the attachment interface 1021. The emitted light may be in any suitable portion of the electromagnetic spectrum, e.g. visible, ultraviolet, or infrared.

The arm cart 1050 can include any suitable number of wheels, such as, for example, three or four. The arm cart 1050 can be manually powerable (e.g., by being pushed by a user). In some embodiments, the arm cart 1050 can include electronic brakes such that the arm cart 1050 can independently apply resistance or braking to each of the wheels. Thus, the electronic brakes can control the path of the arm cart 1050 such that the arm cart 1050 (and a coupling mechanism 1039 of the robotic arm 1030) is directed toward the attachment interface 1021 of the surgical table 1000 as the user pushes the arm cart 1050 toward the attachment interface 1021. In some embodiments, the cart 1050 can also have limited speed (i.e., an upper speed limit).

The arm cart 1050 can include one or more light sensors 1051. The one or more light sensors 1051 can emit a beacon and sense a reflection of the beacon off one or both of the light wall barriers 1028A and 1028B. Thus, the arm cart 1050 can automatically maneuver the arm cart 1050 toward the attachment interface 1021 using, for example, the electronic braking, based on the sensed location of one or both of the light wall barriers 1028A and 1028B and/or the sensed distance between the arm cart 1050 and one or both of the light wall barriers 1028A and 1028B. As described above, the light wall barriers 1028A and 1028B can diverge away from the attachment interface 1021, creating a triangularly-shaped barrier. Thus, the light wall barriers 1028A and 1028B can guide the arm cart 1050 with increasing accuracy as the arm cart 1050 maneuvers closer to the surgical table 1000 and the distance between the light wall barriers 1028A and 1028B decreases.

Although the arm cart 1050 and the surgical table 1000 are described such that the one or more light sensors 1051 are disposed on the arm cart 1050 and the first light emitter 1023A and the second light emitter 1023B are disposed on the surgical table 1000, in some embodiments the location of these components can be reversed such that the one or more light sensors 1051 are disposed on the surgical table 1000 and the first light emitter 1023A and the second light emitter 1023B are disposed on the arm cart 1050.

The surgical table 1000 can also include a close range motion sensor 1083. The close range motion sensor 1083 can be mounted in or near the attachment interface 1021. The close range motion sensor 1083 can determine if foreign items will inhibit attachment of the coupling mechanism 1039 of the robotic arm 1030 to the attachment interface 1021. The close range motion sensor 1083 can then communicate to the arm cart 1050 that attachment of the robotic arm 1030 will be impeded (e.g., blocked by a drape). In some embodiments, the close range motion sensor 1083, upon sensing a potential obstruction to the coupling of the coupling mechanism 1039 to the attachment interface 1021, can signal the arm cart 1050 to stop moving (or to stop moving the robotic arm 1030) toward the attachment interface 1021. The close range motion sensor 1083 can then pause the coupling operation and can warn a user of the potential obstruction. In some embodiments, the close range motion sensor 1083 can also sense the removal of the potential obstruction and signal the arm cart 1050 to resume the coupling operation.

Figure 8B:
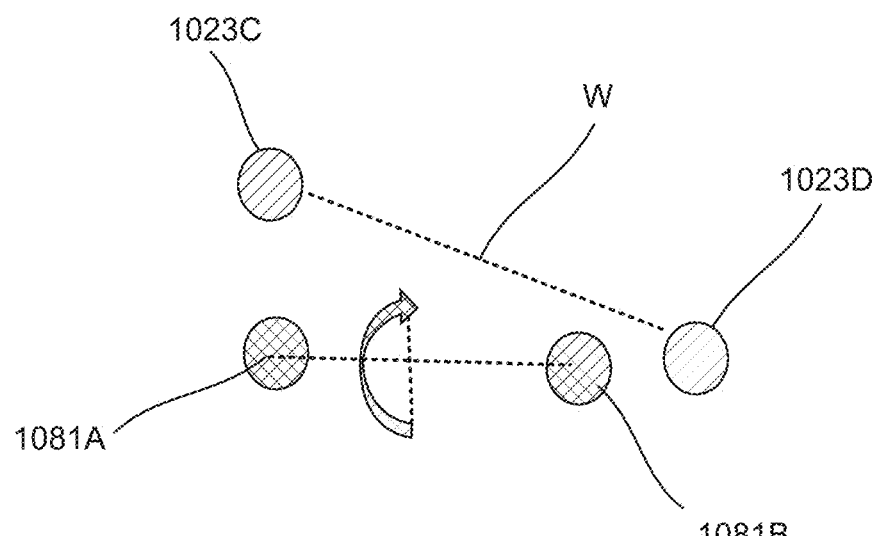

As shown schematically in FIG. 8B, the surgical table 1000 can also include a third light emitter 1023C and a fourth light emitter 1023D. These emitters 1023C, 1023D can be used to indicate the orientation of the top of the surgical table 1000, i.e. the orientation of the attachment interface 1021, as indicated by axis W shown in FIG. 8B. The arm cart 1050 and/or the robotic arm 1030 can include a detector, such as detectors 1081A and 1081, to sense the light from the emitters, and use internal orientation hardware to rotate and/or translate the coupling mechanism 1039 of the robotic arm 1030 such that the orientation of the coupling mechanism 1039 matches the orientation of the attachment interface 1021. Although the elements 1081A and 1081B of FIG. 8B are described as detectors, in some embodiments elements 1081A and 1081B are representative of two portions of the coupling mechanism and the detectors are disposed on a different portion of the arm cart 1050 and/or the robotic arm 1030 than the coupling mechanism 1039. In such embodiments, the detectors can be used to align elements 1081A and 1081B with the attachment interface 1021.

In some embodiments, after the macro-alignment procedure described above with reference to FIGS. 8A and 8, the surgical table 1000 and the arm cart 1050 and/or the robotic arm 1030 can be further aligned via a micro-alignment procedure, for example using a sensing mechanism operable over a short distance. For example, after the robotic arm 1030 has been disposed in close proximity to the attachment interface 1021 via alignment of the arm cart 1050 as described above, a sensor can be used on the coupling mechanism 1039 of the robotic arm 1030 and/or on the attachment interface 1021 of the surgical table 1000 to precision guide the coupling mechanism 1039 of the robotic arm 1030 into engagement with the attachment interface 1021. Suitable sensors could include, for example, Hall effect sensors.

Figure 9A:
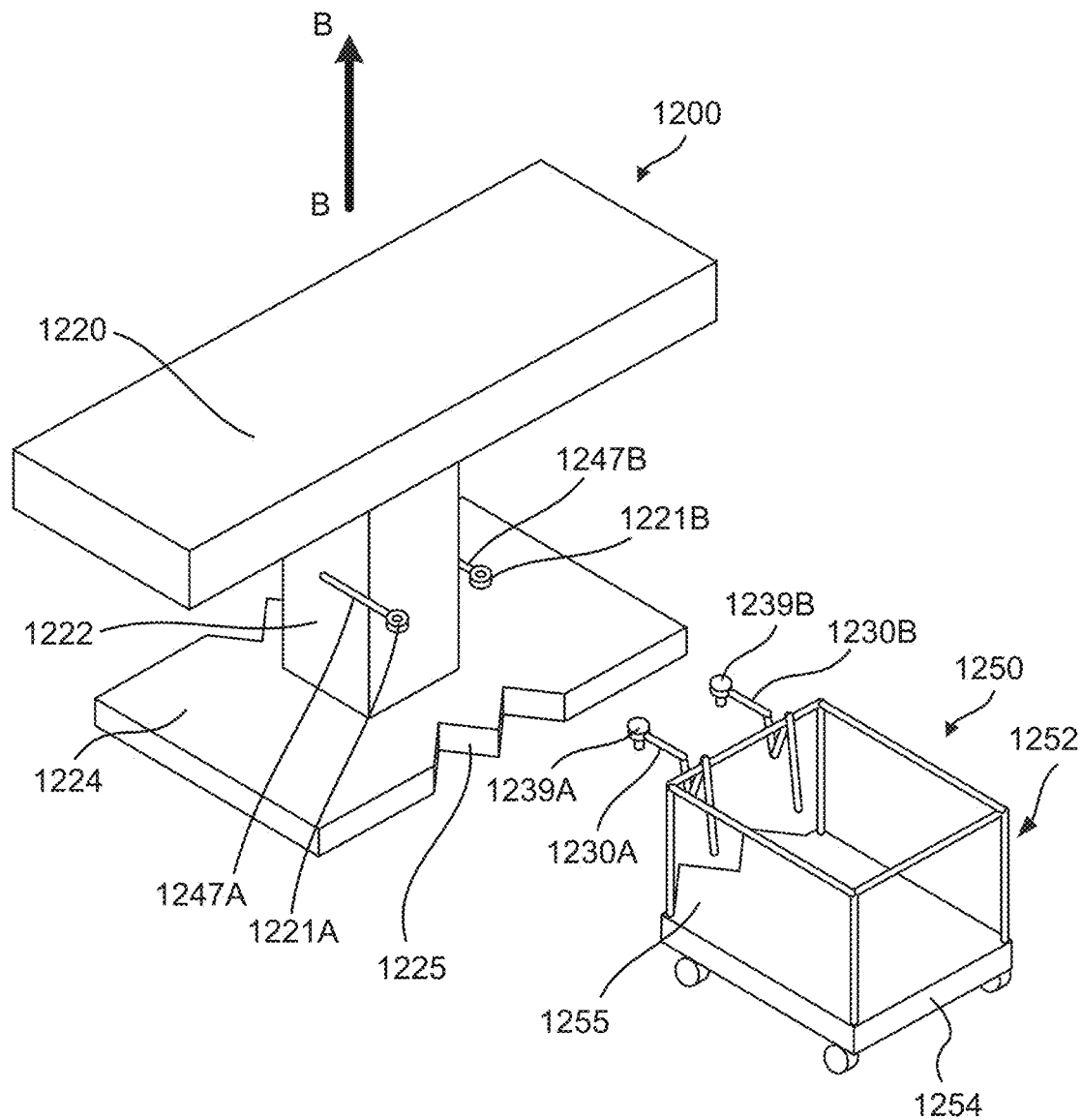
FIGS. 9A-9C are schematic illustrations of a surgical table and an arm cart in a kneeling position, an engagement position, and an operating position, respectively, according to an embodiment.
Figure 9B:
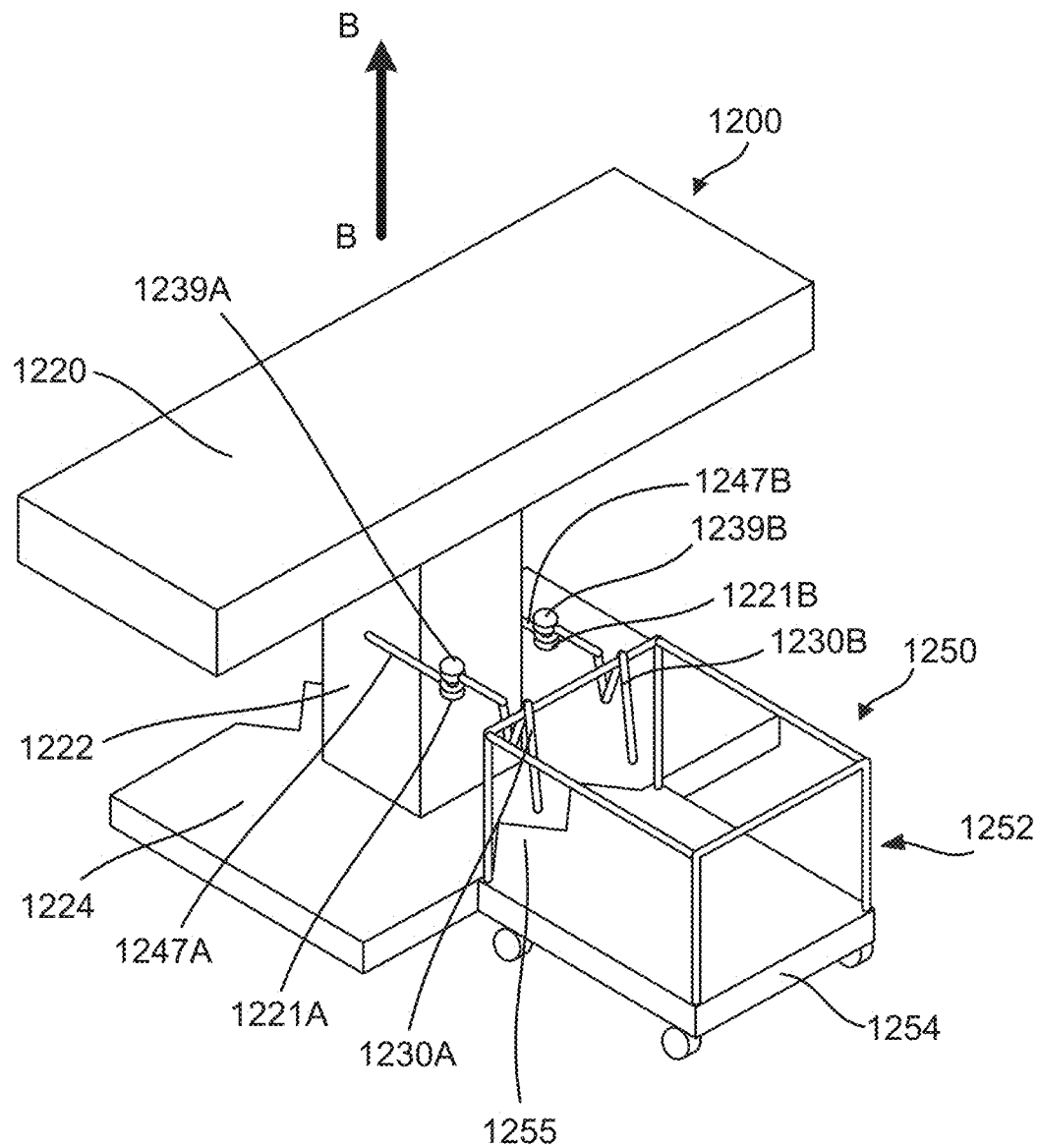
Figure 9C:
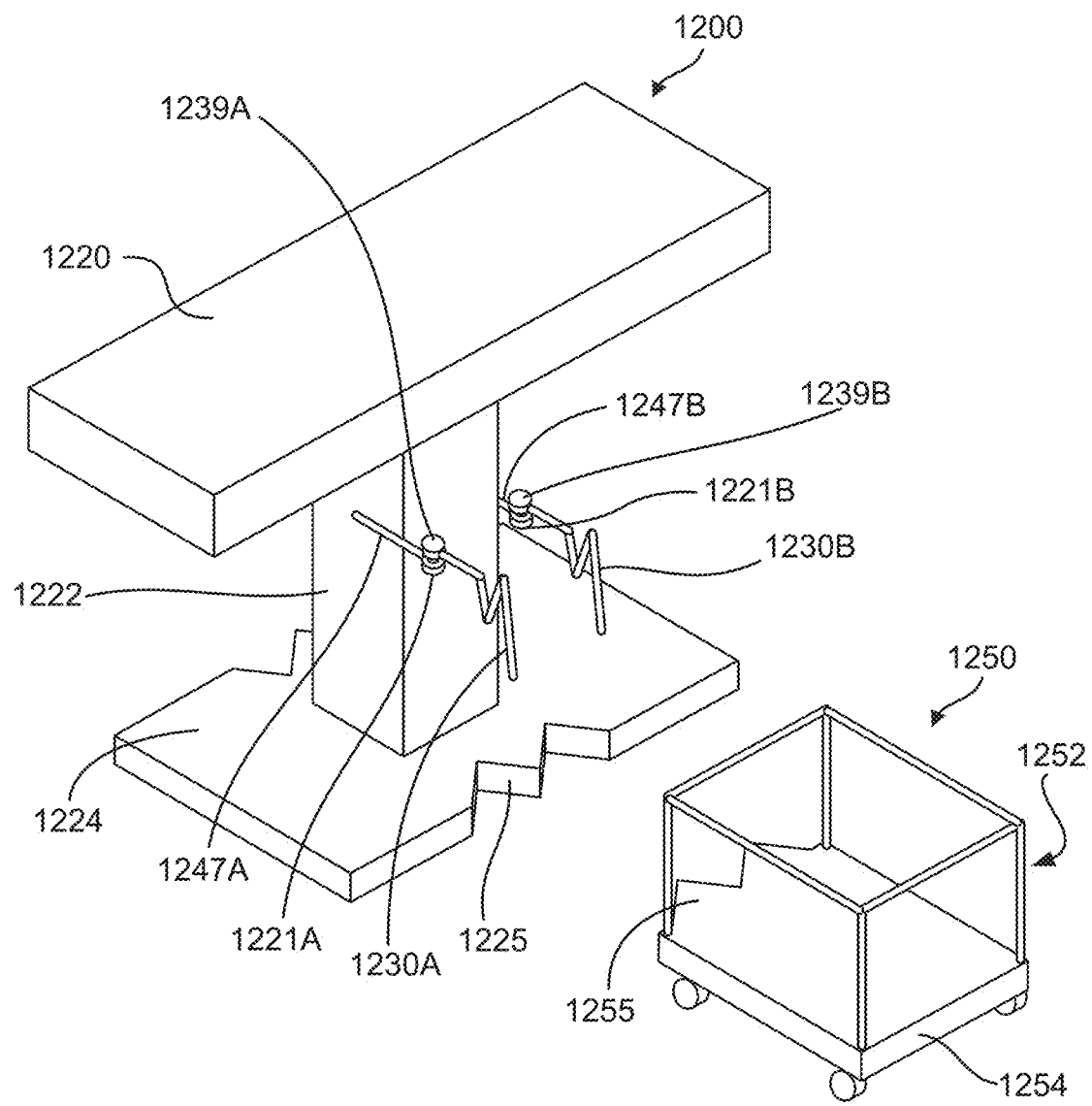

FIGS. 9A-9C are schematic illustrations of a surgical table 1200 and an arm cart 1250. The arm cart 1250 can be the same or similar in structure and/or function to any of the arm carts described herein. For example, the arm cart 1250 can include an arm container 1252 and a base 1254. The arm container 1252 is configured to support, protect, and promote sterility for one or more robotic arms 1230 (e.g., first robotic arm 1230A and optional second robotic arm 1230B) during transportation of the one or more robotic arms 1230, for example, from a storage area to the operating area, and during transfer of the one or more robotic arms 1230 from the arm cart 1250 to the surgical table 1200 for use during a surgical procedure. The one or more robotic arms 1230 can be the same or similar in structure and/or function to any of the robotic arms described herein. The one or more robotic arms 1230 can each include an arm coupling mechanism 1239 (e.g., first arm coupling mechanism 1239A and second arm coupling mechanism 1239B). While the one or more robotic arms 1230 are stored and/or transported by the arm cart 1250, the one or more robotic arms 330 can be mostly, substantially completely, or completely maintained within the footprint of the arm cart 1250 such that the one or more robotic arms 1230 will be less likely to be accidentally bumped or damaged. In some embodiments, the arm container 1252 can be structured as a vertically-extending protection frame that, in combination with the base 1254, defines a space for storing the one or more robotic arms 1230. In some embodiments, when the one or more robotic arms 1230 are stored within the arm cart 1250, the robotic arms can be maintained within the perimeter of the base 1254, but may extend beyond the perimeter of the arm container 1252.

The surgical table 1200 can be the same or similar in structure and/or function to any of the surgical tables described herein. For example, the surgical table 1200 can include a table top 1220, a table support 1222, and a table base 1224. The table top 1220 has an upper surface on which a patient (not shown) can be disposed during a surgical procedure. The table top 1220 is disposed on the support 1222, which can be, for example, a pedestal, at a suitable height above the floor. The support 1222 (also referred to herein as a pedestal) may provide for movement of the table top 1220 in a desired number of degrees of freedom, such as translation in the Z axis (height above the floor), Y axis (along the longitudinal axis of the table), and/or X axis (along the lateral axis of the table), and/or rotation about the Z, Y, and/or X axes. The table top 1220 may also include multiple sections that are movable relative to each other along/about any suitable axes, e.g., separate sections for each of the torso, one or both legs, and/or one or both arms, and a head support section. Movement of the table top 1220 and/or its constituent sections may be performed manually, driven by motors, controlled remotely, or through any other suitable means. The support 1222 for the table top may be mounted to the base 1224, which can be fixed to the floor of the operating room, or can be movable relative to the floor, e.g., by use of wheels (not shown) on the base 1224. The height of the support 1222 can be adjusted, which together with, for example, the motion (e.g., axial (longitudinal) or lateral motion) of the table top 1220, can allow for the table top 1220 to be positioned at a desired surgical site at a certain height above the floor (e.g., to allow surgeon access) and a certain distance from the support 1220. Additionally, the adjustment of the height of the support 1222 can also cause attachment members associated with the support 1222 (e.g., attachment members 1247 described below) to engage with and lift the one or more robotic arms 1230 from the arm cart 1250.

As shown in FIG. 9A, the arm cart 1250 can also include a first mating feature 1255, which can be the same or similar in structure and/or function to the first mating feature 555 described above with reference to FIG. 5A. Similarly, the surgical table 1200 can include a corresponding second mating feature 1225, which can be the same or similar in structure and/or function to the second mating feature 525 described above with reference to FIG. 5A. Thus, the arm cart 1250 can be guided into engagement with the surgical table 1200 such that the first mating feature 1255 is coupled with the second mating feature 1225. As a result of the first mating feature 1255 being coupled with the second mating feature 1225, the arm cart 1250 can be positioned and maintained in a certain position relative to the surgical table 1200 for transfer of the one or more robotic arms 1230 from the arm cart 1250 to the surgical table 1200.

The surgical table 1200 can include one or more attachment members 1247 (e.g., a first attachment member 1247A and a second attachment member 1247B). Each of the one or more attachment members 1247 can include, for example, an extension arm. A first end of each of the one or more attachment members 1247 can be coupled to the support 1222. The one or more attachment members 1247 can each include an attachment interface 1221 disposed at a second end of each of the one or more attachment members 1247. Specifically, as shown in FIG. 9A, the first attachment member 1247A can include a first attachment interface 1221A and the second attachment member 1247B can include a second attachment interface 1221B. The attachment interfaces 1221 can be structured such that the attachment interfaces 1221 can releasably engage with the arm coupling members 1239 (e.g., the first arm coupling member 1239A and the second arm coupling member 1239B). For example, the attachment interfaces 1221 can include a loop-shaped or basket-shaped component. In some embodiments, the attachment interfaces 1221 can be shaped and sized to engage with any of the arm coupling members 1239 of the one or more robotic arms 1230.

The arm coupling members 1239 of the robotic arms 1230 can each be shaped and sized such that one or more of the attachment interfaces 1221 can releasably engage with and move each of the arm coupling members 1239. For example, the first attachment interface 1221A can be positioned under the first arm coupling member 1239A such that the first attachment member 1221A is aligned with the first arm coupling member 1239A in the X and Y directions. The first attachment interface 1221A can then be moved vertically (via, for example, vertical movement of the support 1222) into engagement with the first arm coupling member 1239A. For example, the first attachment interface 1221A can define an opening and can be raised until the first attachment interface 1221A is disposed in a surrounding relationship with a first portion of the first arm coupling member 1239A. The first attachment interface 1221A can engage with a second portion of the first arm coupling member 1239A such that further vertical movement of the first attachment interface 1221A causes movement of the first arm coupling member 1239A (and thus the first robotic arm 1230A).

Although two attachment members 1247 are shown in FIG. 9A, any suitable number of attachment members can be included, such as, for example, one, three, or four. Additionally, although the structure of the attachment interfaces 1221 is described as a loop or a basket, the attachment interfaces 1221 can be any suitable shape and can include any suitable engagement features such that the attachment interfaces 1221 can capture an arm coupling member, such as the arm coupling members 1239.

In use, as shown in FIG. 9A, the surgical table 1200 can be in a first, kneeling configuration, in which the attachment members 1247 (and thus the attachment interfaces 1221) are positioned vertically lower than the arm coupling members 1239 of the robotic arms 1230. The arm cart 1250 can be in a first location remote from the surgical table 1200. The first robotic arm 1230A and the second robotic arm 1230B can be disposed on the arm cart 1250 in a deployed configuration such that the first coupling mechanism 1239A and the second coupling mechanism 1239B are disposed for engagement with the first attachment interface 1221A and the second attachment interface 1221B, respectively, upon alignment along the X axis and the Y axis.

The arm cart 1250 can be moved toward the surgical table 1200. As shown in FIG. 9B, when the arm cart 1250 is properly positioned relative to the attachment members 1247 (e.g., the first mating feature 1255 is engaged with the second mating feature 1225), the support 1222 can be manipulated to extend vertically along line B-B (i.e. move from the kneeling position to an engagement position). Thus, the attachment members 1247 can be moved vertically along line B-B via movement of the support 1222 into engagement with the arm coupling members 1239. More specifically, the first attachment interface 1221A can engage with the first arm coupling member 1239A and the second attachment interface 1221B can engage with the second arm coupling member 1239B. In some embodiments, the attachment members 1247 remain in the same position relative to the table top 1220 through all vertical positions of the table top 1220 as a result of extension or retraction of the support 1222.

Figure 10A:
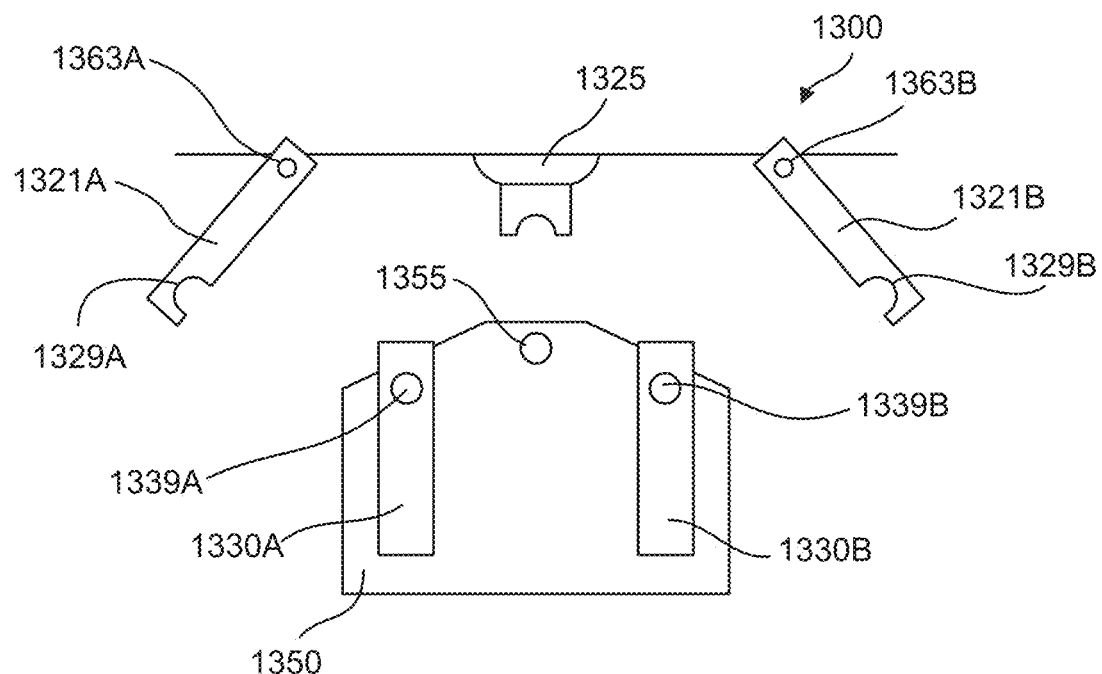
FIG. 10A-10C are schematic illustrations of a surgical table and a robotic arm in a disengaged configuration, a registered configuration, and a latched configuration, respectively, according to an embodiment.
Figure 10B:
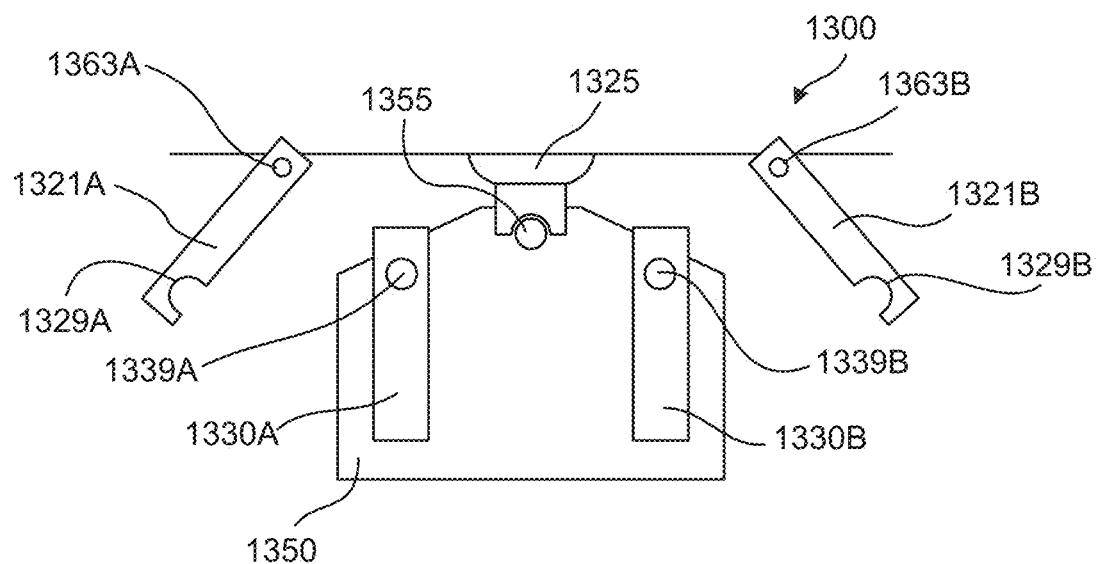
Figure 10C:
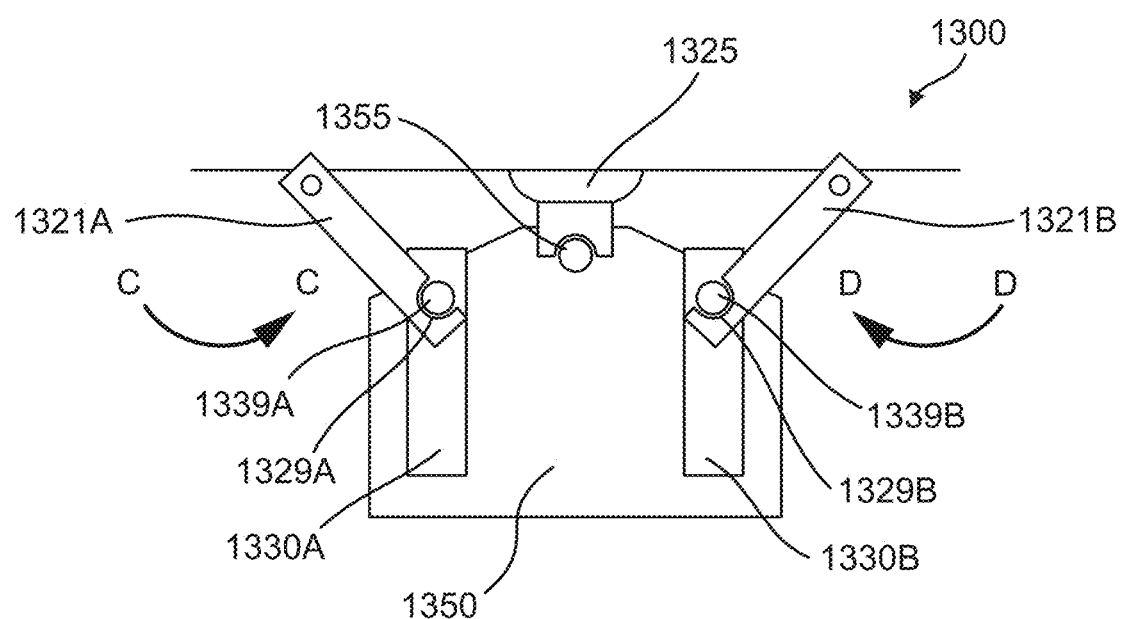

After the attachment members 1247 are engaged with the arm coupling members 1239, the support 1222 can be manipulated to extend vertically farther along line B-B such that the attachment members 1247 rise vertically farther relative to the base 1224 and the arms cart 1250 (i.e., move from the engagement position to an operating position). The upward vertical movement of the attachment members 1247, which are engaged with the arm coupling members 1239 via the attachment interfaces 1221, lifts the robotic arms 1230 out of the arm cart 1250, as shown in FIG. 9C. The robotic arms 1230 are then engaged with the surgical table 1200 via the attachment members 1247 and can be used for a surgical procedure. As shown in FIG. 10C, the arm cart 1250 can then be moved away from the surgical table 1200.

Although the robotic arms 1230 are shown as being loaded on the arm cart 1250 in a deployed configuration (i.e., the coupling mechanisms 1239 exposed for engagement by the attachment members 1247) for transport via the arm cart 1250 to the surgical table 1200 in FIG. 9A, in some embodiments the robotic arms 1230 can be stored within the arm cart 1250 and moved to the deployed configuration. In some embodiments, the arm cart 1250 can manipulate the configuration of the robotic arms 1230 such that the arm coupling members 1239 are exposed and accessible by the attachment members 1247. In some embodiments, the attachment members 1247 can pivot or rotate from stowed positions to use positions prior to moving into engagement with the arm coupling members 1239. Although FIGS. 9A-9C show both robotic arms (i.e., robotic arm 1230A and robotic arm 1230B) being lifted from the arm cart 1250 by the attachment members 1247 simultaneously, in some embodiments only one robotic arm 1230 can be engaged and lifted from the arm cart 1250. For example, only one robotic arm 1230 can be positioned in a deployed configuration for engagement by an attachment member 1247 or the arm cart 1250 can position only one coupling mechanism 1239 in X and Y axis alignment with an attachment member 1247. One or more additional robotic arms 1230 can remain in the arm cart 1250 to be used at a later time.

In some embodiments, a surgical table can include an alignment feature with an arm cart and attachment members capable of pivoting into engagement with one or more robotic arms. For example, FIGS. 10A, 10B, and 10C are schematic illustrations of a surgical table 1300, an arm cart 1350, and robotic arms 1330 (e.g., first robotic arm 1330A and second robotic arm 1330B) in a disengaged configuration, a registered configuration, and a latched configuration, respectively. The surgical table 1300 and the arm cart 1350 can be the same or similar in structure and/or function to any of the surgical tables and arm carts described herein, respectively. Similarly, the first and second robotic arms 1330A and 1330B can be the same or similar to any of the robotic arms described herein. The surgical table 1300 can include a first mating feature 1325 and the arm cart 1350 can include a complementary second mating feature 1355. The first mating feature 1325 can be configured to engage with and/or receive the second mating feature 1355.

The first robotic arm 1330A can include a first coupling mechanism 1339A and the second robotic arm 1330B can include a second coupling mechanism 1339B. The surgical table 1300 can include a first attachment member 1321A and a second attachment member 1321B. The first attachment member 1321A and the second attachment member 1321B can be rotationally coupled to the surgical table 1300 via a first pivot joint 1363A and a second pivot joint 1363B, respectively. The first attachment member 1321A can define and/or include a first engagement feature 1329A. The second attachment member 1321B can define and/or include a second engagement feature 1329B. The first engagement feature 1329A can be shaped and sized such that the first engagement feature 1329A can engage with and/or receive the first coupling mechanism 1339A. The second engagement feature 1329B can be shaped and sized such that the second engagement feature 1329B can engage with and/or receive the second coupling mechanism 1339B. Thus, the first attachment member 1321A and the second attachment member 1321B can be rotated via the first pivot joint 1363A and the second pivot joint 1363B along lines C-C and D-D into engagement with the first coupling mechanism 1339A and the second coupling mechanism 1339B of the first robotic arm 1330A and the second robotic arm 1330B, respectively. In some embodiments, the pivot positions of the first attachment member 1321A and the second attachment member 1321B can be electronically controlled such as, for example, via sensors. For example, the first mating feature 1325 can include a sensor configured to sense engagement between the coupling member first mating feature 1325 and the second mating feature 1355 such that the first attachment member 1321A and the second attachment member 1321B automatically pivot along lines C-C and D-D upon engagement between the first mating feature 1325 and the second mating feature 1355. In some embodiments, the pivot positions of the first attachment member 1321A and the second attachment member 1321B can be controlled manually by a user. In some embodiments, the first attachment member 1321A and the second attachment member 1321B can be biased such that, upon release of the first attachment member 1321A and the second attachment member 1321B from the configuration shown in FIG. 10B, the first attachment member 1321A and the second attachment member 1321B rotate to the position shown in FIG. 10C.

In use, the arm cart 1350 can be moved near the surgical table 1300, as shown in FIG. 10A, via, for example, wheels coupled to the bottom of the arm cart 1350. The arm cart 1350 can be manipulated to align and engage the second mating feature 1355 of the arm cart 1350 with the first mating feature 1325 of the surgical table 1300, as shown in FIG. 10B. Upon engagement between the second mating feature 1355 of the arm cart 1350 with the first mating feature 1325 of the surgical table 1300, the first attachment member 1321A can be rotated along line C-C such that the first engagement feature 1329A latches with the first coupling mechanism 1339A of the first robotic arm 1330A, as shown in FIG. 10C. Similarly, the second attachment member 1321B can be rotated along line D-D such that the second engagement feature 1329B latches with the second coupling mechanism 1339B of the second robotic arm 1330B. After latching, the first attachment member 1321A can rotate the first robotic arm 1330A out of the stowed position on the arm cart 1350 and the second attachment member 1321B can rotate the second robotic arm 1330B out of the stowed position on the arm cart 1350. Thus, the first robotic arm 1330A and/or the second robotic arm 1330B can be securely coupled to the surgical table 1300 and can be transitioned to an operative position (i.e., disengaged from the arm cart) from a stowed position on the arm cart 1350. In some embodiments, the first attachment member 1321A and the second attachment member 1321B can engage with and rotate the first robotic arm 1330A and the second robotic arm 1330B, respectively, simultaneously or sequentially.

Figure 11:
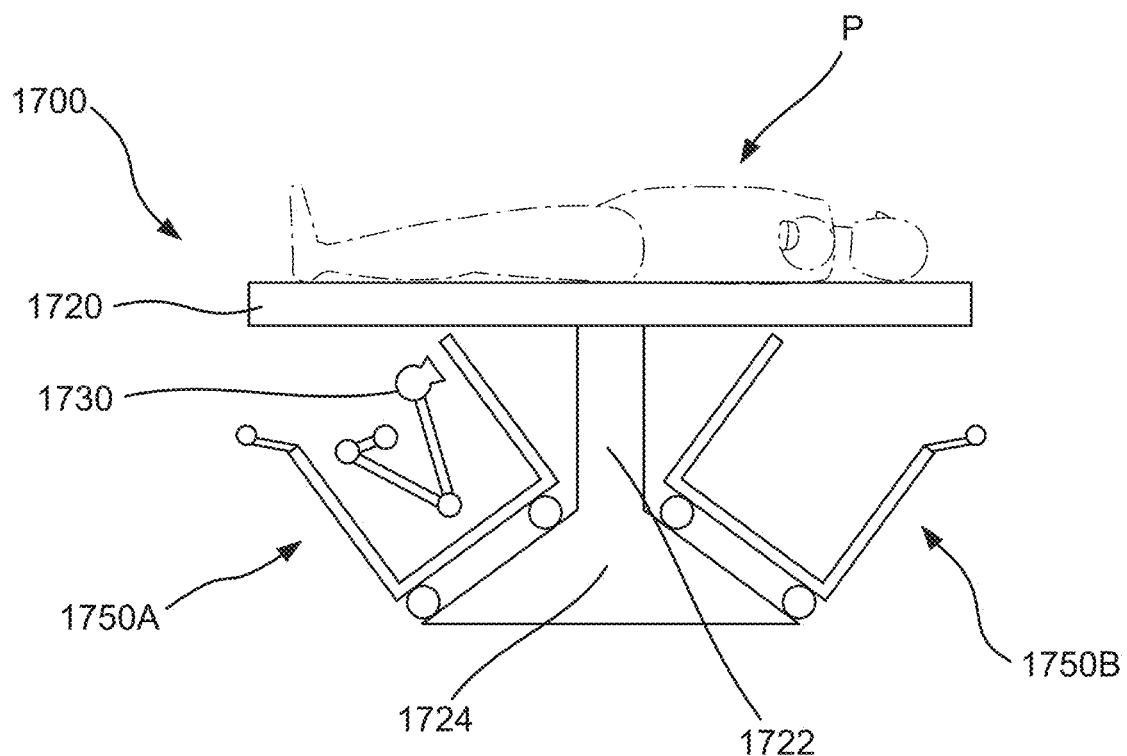
FIG. 11 is a schematic illustration of two arm carts docking under opposite ends of a surgical table, according to an embodiment.

FIG. 11 is a side view of a surgical table 1700 with a first arm cart 1750A and a second arm cart 1750B in a nested configuration under the surgical table 1700. The surgical table 1700 can be the same or similar in structure and/or function to any of the surgical tables described herein. For example, the surgical table 1700 can include a table top 1720, a support 1722, and a base 1724. The first arm cart 1750A and the second arm cart 1750B can be the same or similar in structure and/or function to any of the arm carts described herein. For example, the first arm cart 1750A is shown containing a robotic arm 1730. To enable arm carts 1750A, 1750B to be easily moved into the stored or nested configuration under the table top 1720 of table 1700, the base 1724 of table is configured with an inclined upper surface. Thus, each of the first arm cart 1750A and the second arm cart 1750B can be rolled up the incline of the base 1724 into their respective stored configurations under the table top 1720. A suitable retention mechanism (not shown in FIG. 11) such as, for example, one or more detents, can be used to hold each arm cart in the stored configuration, i.e. prevent the arm cart from rolling down the inclined upper surface of base 1724. In some embodiments, each arm cart, and the table, can be configured such that the cart can be placed in the stored configuration with an arm contained within the cart, as shown in FIG. 11 with first arm cart 1750A and arm 1730. The cart and arm may thus be placed under the table top 1720 before a procedure, then moved to a suitable position for docking with the table and attachment of the arm 1730 to the table 1700, as described above. The empty cart may then be returned to the stored configuration. In other embodiments, the cart is not configured to be stored under the table while it contains an arm, and instead may only be placed in the stored configuration when empty.

Figure 12A:
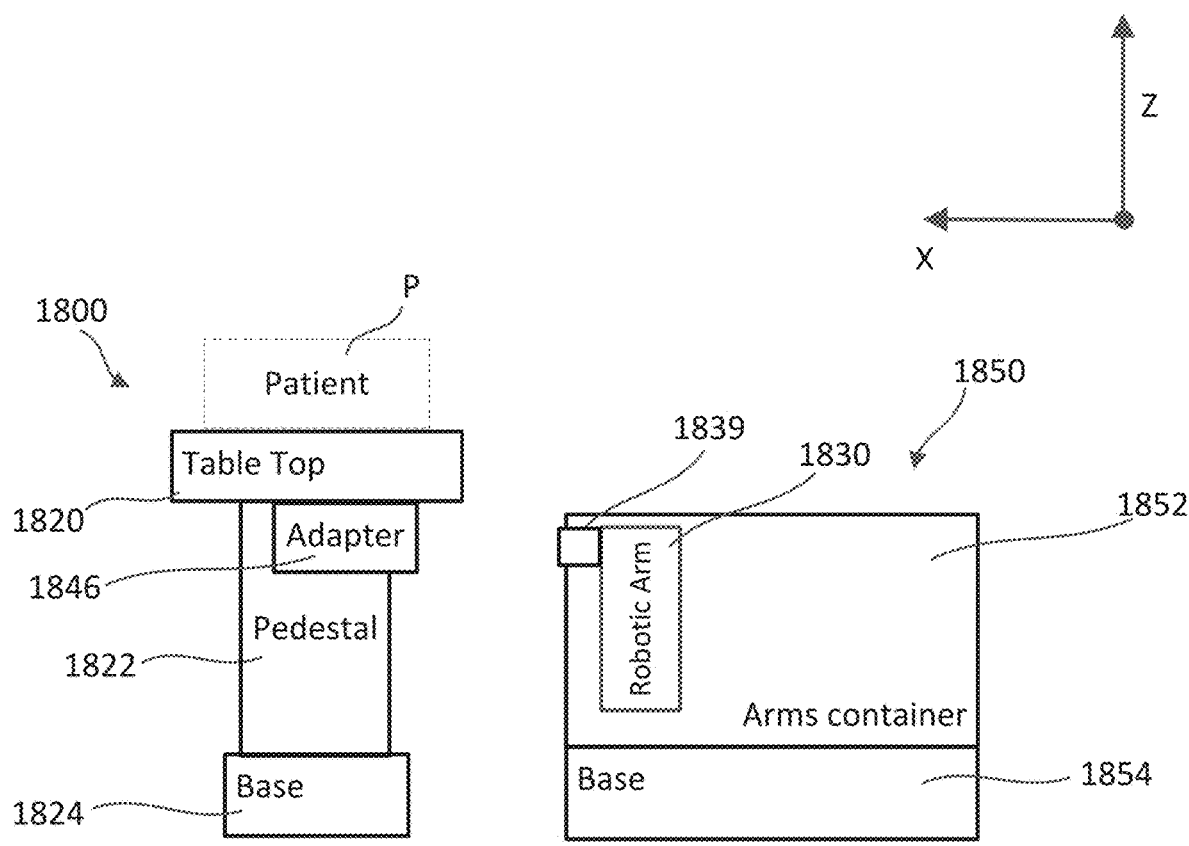
FIGS. 12A-12H are schematic illustrations of an arm cart containing a robotic arm in a variety of positions relative to a surgical table, according to an embodiment.
Figure 12B:
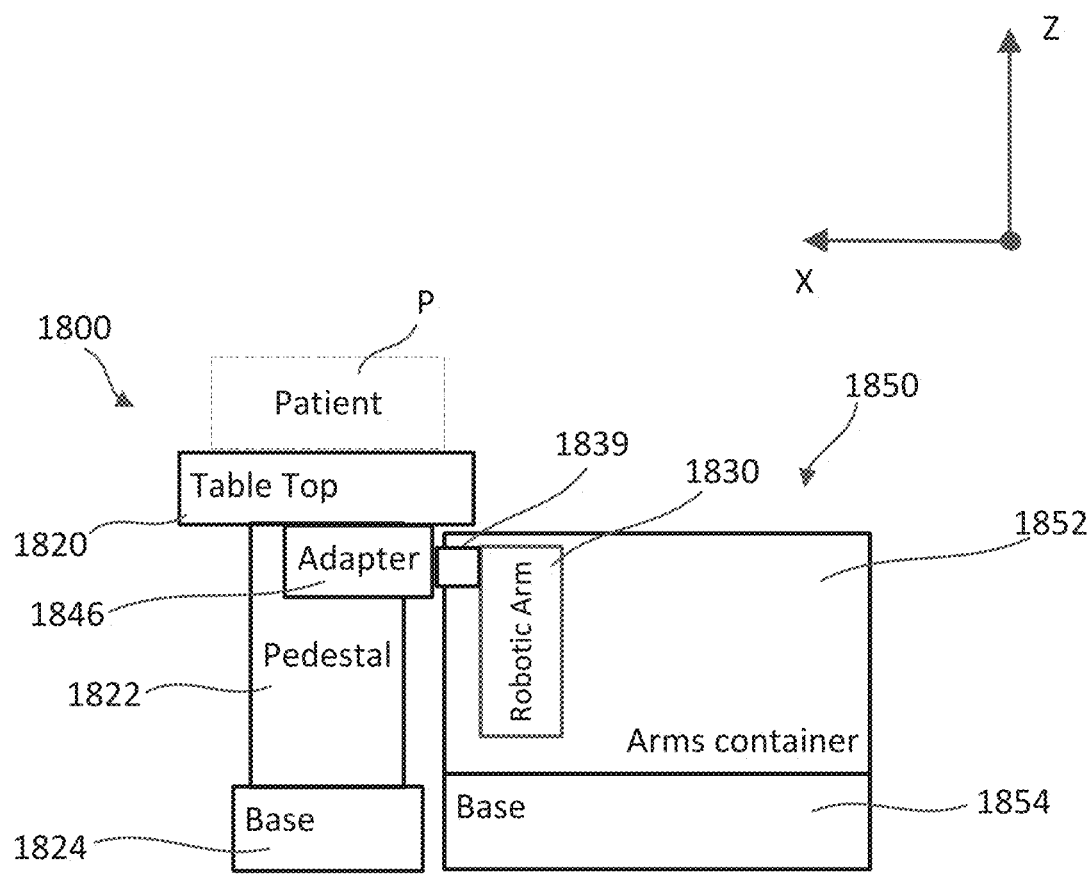

In some embodiments, a robotic arm can be transported via an arm cart in the same pose and/or orientation in which the robotic arm can be transferred to a surgical table and stowed under the surgical table. Thus, in some embodiments, the pose and/or orientation of the robotic arm can remain the same during storage and in preparation for and during transfer of the robotic arm to the surgical table. For example, FIGS. 12A-12H are schematic illustrations of a surgical table 1800 and an arm cart 1850. As shown in FIG. 12A, the arm cart 1850 contains and supports a robotic arm 1830. The surgical table 1800, the arm cart 1850, and the robotic arm 1830 can be the same or similar in structure and/or function to any of the surgical tables, arm carts, and robotic arms described herein, respectively. For example, the arm cart 1850 can include an arm container 1852 and a base 1854. The surgical table 1800 can include a table top 1820, a table support 1822, and a table base 1824. The table top 1820 has an upper surface on which a patient P can be disposed during a surgical procedure, as shown schematically in FIG. 12A. The table top 1820 is disposed on the support 1822, which can be, for example, a pedestal, at a suitable height above the floor. The support 1822 can be mounted to the base 1824, which can be fixed to the floor of the operating room or can be moveable relative to the floor, e.g., by use of wheels on the base. Additionally, an adapter 1846 can be coupled to or separate from the surgical table 1800. For example, as shown in FIG. 12A, the adapter 1846 can be coupled to or separate from but engageable with or coupleable to the table top 1820. The robotic arm 1830 can be releasably coupled to the adapter 1846. The robotic arm 1830 can include a coupling mechanism 1839 such that the robotic arm 1830 can couple to an engagement feature (not shown) of the adapter 1846 via the coupling mechanism 1839. Additionally, the adapter 1846 can be configured to move the robotic arm 1830 via the coupling mechanism 1839 without the robotic arm 1830 changing in configuration or orientation relative to the coupling mechanism 1830. For example, the adapter 1846 can rotate the robotic arm 1830 about the Z axis from the arm cart 1850 into a stowed position under the table top 1820 (as shown in FIG. 12E) and/or rotate the robotic arm 1830 about the Z axis and/or the X axis into an operating position (as shown in FIG. 12G).

The arm cart 1850 can be moveable on a support surface relative to the surgical table 1800. For example, as shown in FIG. 12A, the arm cart 1850 can be positioned near the surgical table 1800. The robotic arm 1830 can be arranged in or on the arm cart 1850 such that the coupling mechanism 1839 is properly positioned for engagement with the adapter 1846 upon proper alignment of the arm cart 1850 with the surgical table 1800. As shown in FIG. 12B, the arm cart 1850 can then be moved into alignment and/or engagement with the surgical table 1800 for transfer of the robotic arm 1830 from the arm cart 1850 to the adapter 1846 of the surgical table 1800. In such a position, the coupling mechanism 1839 can be coupled to an engagement feature of the adapter 1846 without the robotic arm 1830 changing configuration or orientation relative to the arm cart 1850.

Figure 12C:
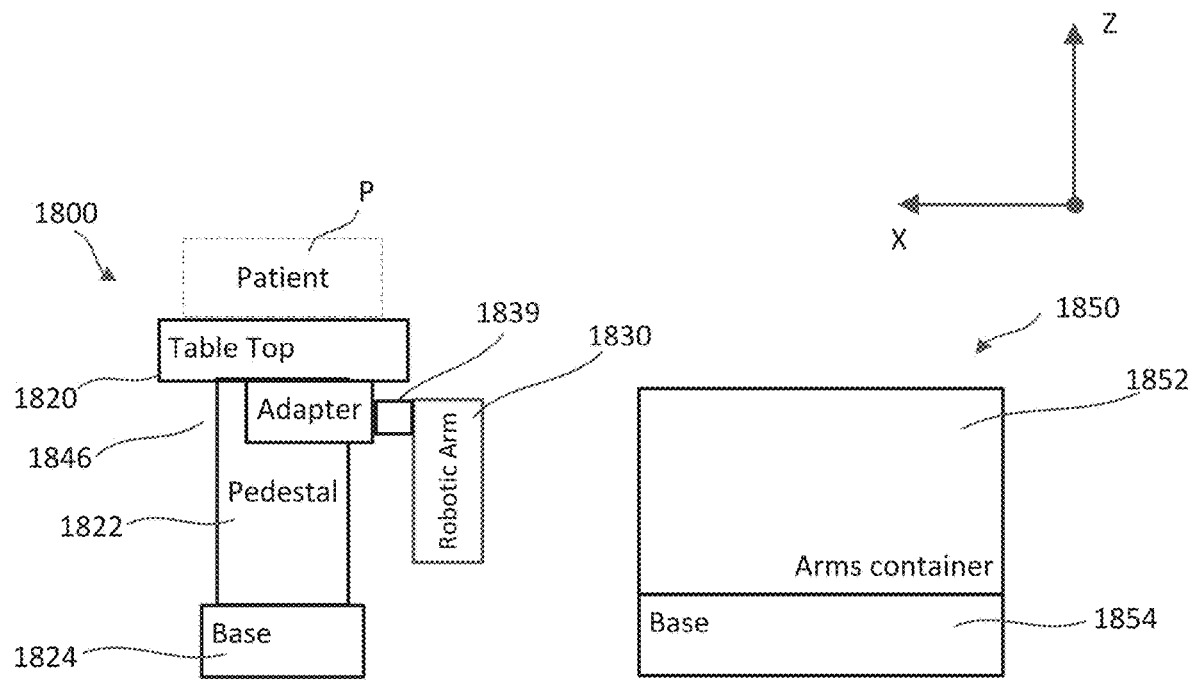
Figure 12D:
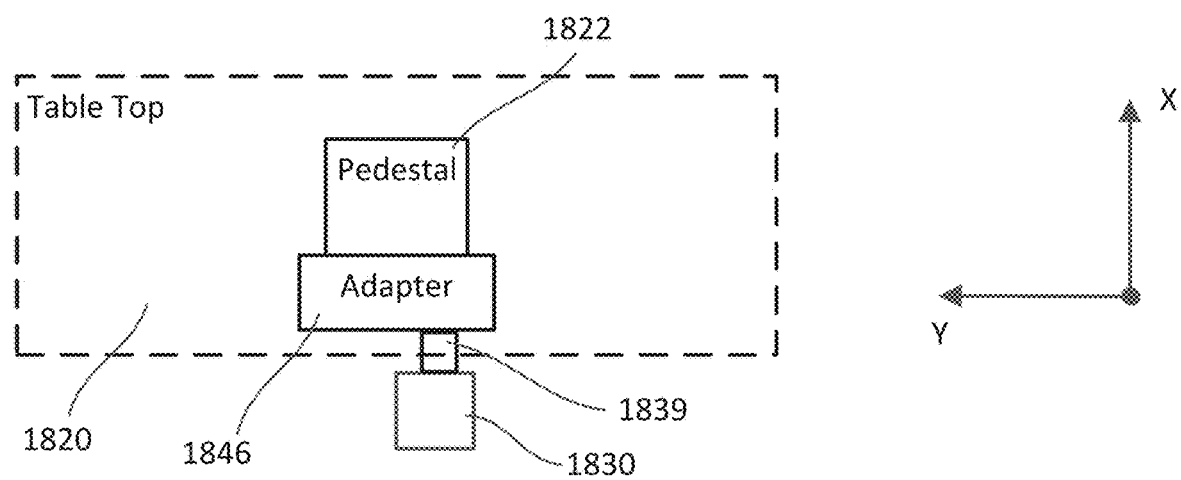
Figure 12E:
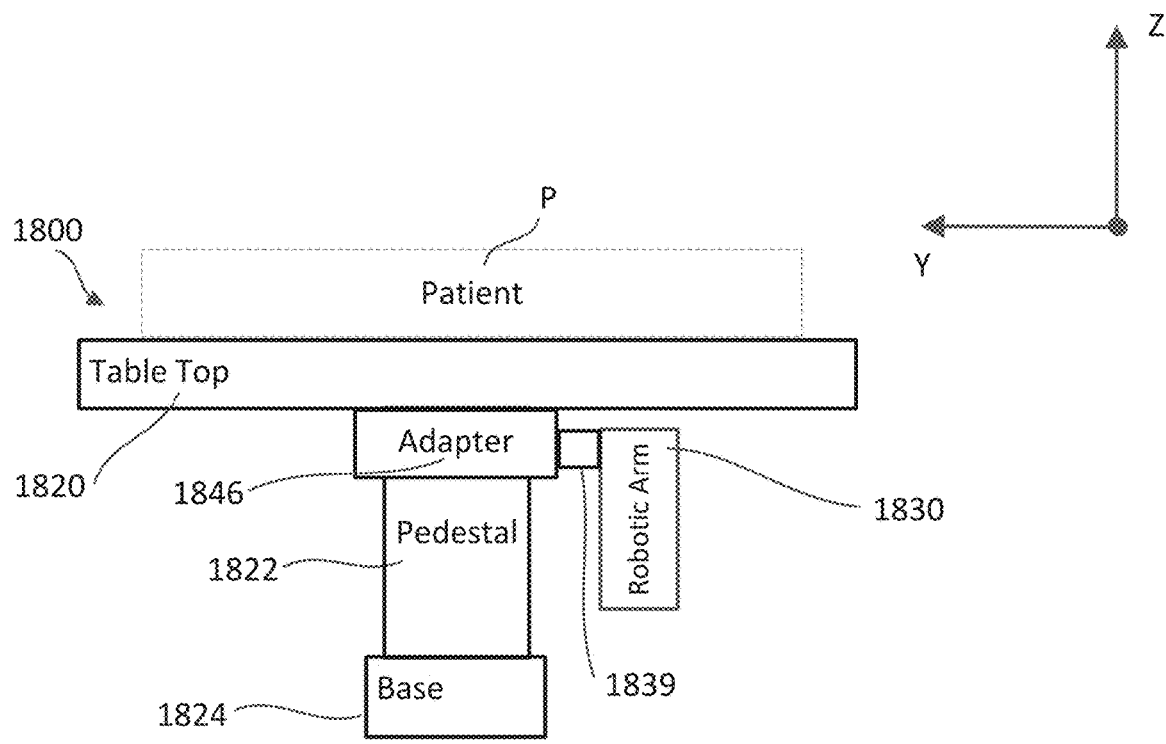

After engagement between the coupling mechanism 1839 and the adapter 1846, the arm cart 1850 can be moved away from the surgical table 1800 and the robotic arm 1830, as shown in FIG. 12C. As shown in FIG. 12D, which is a top view of the surgical table 1800 and the robotic arm 1830 with the table top 1820 shown in phantom, upon movement of the arm cart 1850 away from the surgical table 1800, the robotic arm 1830 can be supported by the adapter 1846 in transfer position in which the robotic arm 1830 extends away from the table along the X axis.

Figure 12F:
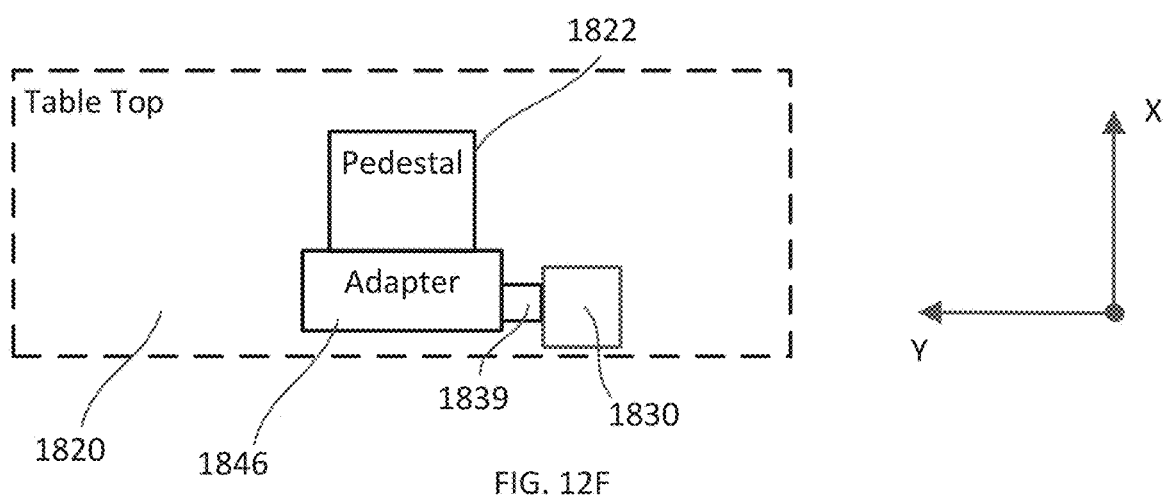
Figure 12G:
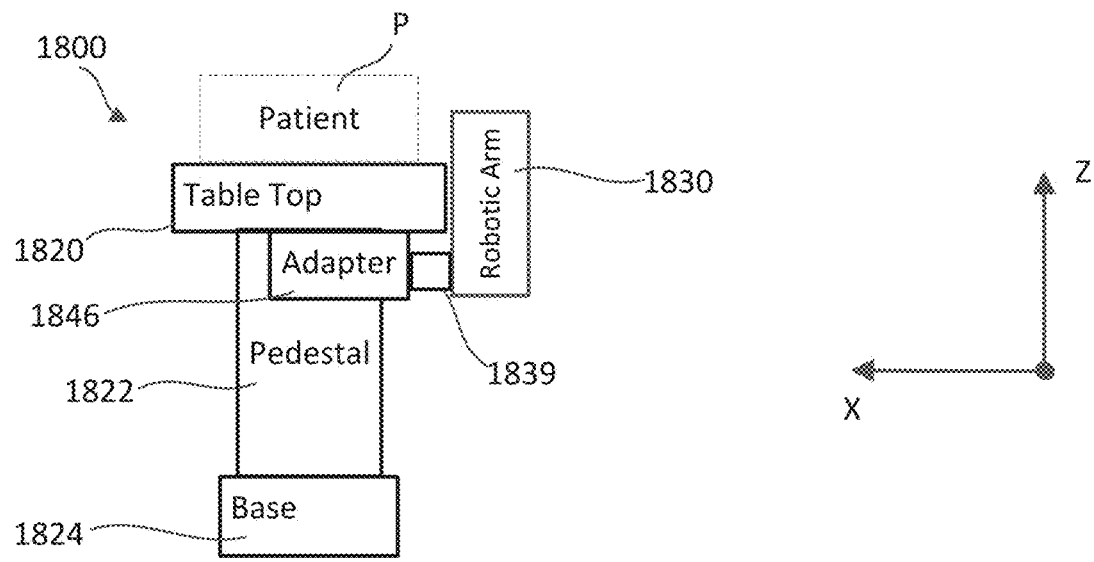

As shown in FIGS. 12E and 12F, which are a front view and a top view, respectively, of the surgical table 1800 and the robotic arm 1830, the adapter 1846 can rotate the robotic arm 1830 from the transfer position shown in FIGS. 12C and 12D to a stowed position under the table top 1820. During the rotation of the robotic arm 1830 from the transfer position to the stowed position and while maintained in the stowed position, the robotic arm 1830 can maintain the same configuration.

Figure 12H:
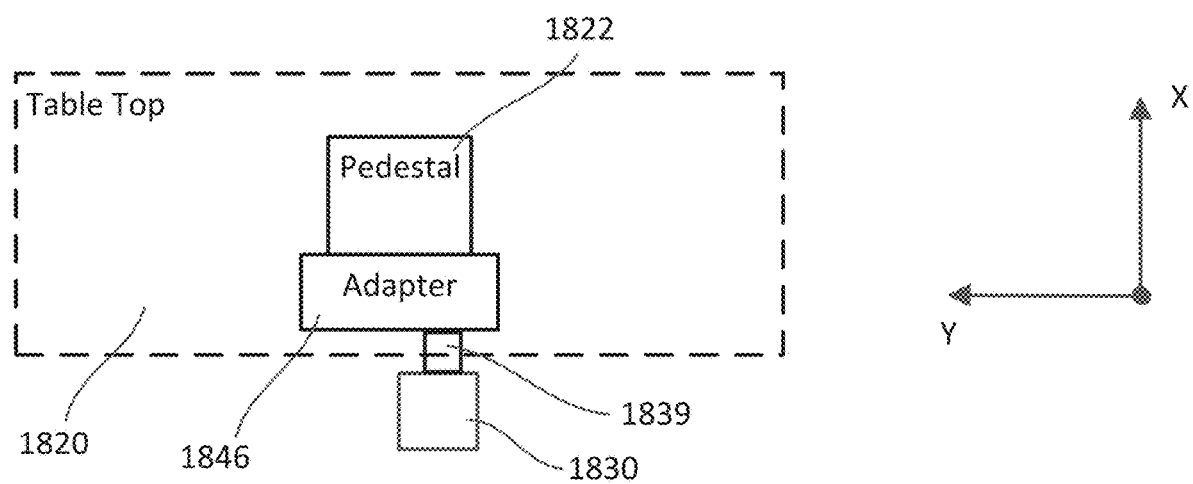

As shown in FIGS. 12G and 12H, which are a side view and a top view, respectively, of the surgical table 1800 and the robotic arm 1830, the adapter 1846 can also rotate the robotic arm 1830 from the stowed position to an operating position. In some embodiments, the adapter 1846 can first rotate the robotic arm 1830 about the Z axis until the robotic arm 1830 is in the original transfer position. The adapter 1846 can then rotate the robotic arm 1830 about the X axis such that the robotic arm 1830 extends above the table top 1820. During rotation about the Z axis and the X axis, the robotic arm 1830 can maintain the same configuration. In some embodiments, the adapter 1846 can first rotate the robotic arm 1830 about the Z axis until the robotic arm 1830 is in the original transfer position. The configuration of the robotic arm can then change such that the robotic arm 1830 can access the top surface of the table top 1820 and/or the patient P disposed on the tabletop 1820.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The invention claimed is:

1. A cart comprising:
   a robotic arm having a coupler; and
   a light sensor configured to sense that the cart is positioned adjacent to a surgical table for engagement of the coupler with the surgical table in response to receiving a light signal.

2. The cart of claim 1, wherein when the light sensor receives the light signal, the coupler of the robotic arm is disposed in an engagement relationship with a coupler of the surgical table.

3. The cart of claim 2, wherein the cart is configured to move towards the coupler of the surgical table based on the light signal received by the light sensor.

4. The cart of claim 1, wherein the light signal is an image projected onto a surface by the surgical table.

5. The cart of claim 4, wherein the light sensor senses that the cart is positioned adjacent to the surgical table based on a property of the image that changes when the cart is positioned relative to the surgical table for engagement of the coupler with the surgical table.

6. The cart of claim 5, wherein the property is a color of the image.

7. The cart of claim 1, wherein the light sensor is a first light sensor that is positioned on a first side of the cart, wherein the cart further comprises a second light sensor that is positioned on a second side of the cart that is opposite of the first side.

8. A method for coupling a robotic arm to a surgical table, the method comprising:
   moving the robotic arm cart having a robotic arm coupled thereto, to a location proximate to the surgical table;
   receiving light emitted by the surgical table indicating the position of the cart relative to the surgical table for engagement of a coupler of the robotic arm with the surgical table;
   coupling the coupler of the robotic arm to the surgical table; and
   uncoupling the robotic arm from the cart.

9. The method of claim 8 further comprising moving the cart towards the surgical table in response to the light signal being received from the surgical table.

10. The method of claim 8, wherein the coupler is coupled to a coupler of the surgical table, wherein the method further comprises moving the coupler of the robotic arm towards the coupler of the surgical table based on the light signal received from the surgical table.

11. The method of claim 10, wherein the coupler of the robotic arm is moved such that it is vertically aligned with the coupler of the surgical table, wherein the surgical table comprises a support, wherein coupling comprises translating the support of the surgical table vertically upward such that the coupler of the surgical table translates vertically into engagement with the coupler of the robotic arm.

12. The method of claim 8, wherein the light signal is an image projected on a surface by the surgical table.

13. The method of claim 12, wherein a property of the image is configured to change when the cart is positioned relative to the surgical table for engagement of the coupler of the robotic arm with the surgical table.

14. The method of claim 13, wherein the property is color.

15. The method of claim 8, wherein receiving light comprises perceiving a light beam associated with the surgical table being projected onto a target disposed on the cart, the projection of the light beam onto the target indicating that the coupler of the robotic arm is positioned for engagement with the surgical table.

16. A system comprising:
   a robotic arm comprising a coupler;
   a surgical table; and
   a cart having the robotic arm coupled thereto, comprising a light sensor configured to sense that the cart is positioned adjacent to the surgical table for engagement of the coupler with the surgical table in response to receiving a light signal.

17. The system of claim 16, wherein when the light sensor receives the light signal, the coupler of the robotic arm is disposed in an engagement relationship with a coupler of the surgical table.

18. The system of claim 17, wherein the cart is configured to move towards the coupler of the surgical table based on the light signal received by the light sensor.

19. The system of claim 16, wherein the light signal is an image projected onto a surface by the surgical table.

20. The system of claim 19, wherein the light sensor senses that the cart is positioned adjacent to the surgical table based on a property of the image that changes when the cart is positioned relative to the surgical table for engagement of the coupler with the surgical table.

21. The system of claim 20, wherein the property is a color of the image.

* * * * *